(12) United States Patent
Brutinel et al.

(10) Patent No.: US 12,054,766 B2
(45) Date of Patent: Aug. 6, 2024

(54) DEVICES AND METHODS FOR SAMPLE PARTITIONING AND ANALYSIS

(71) Applicant: NEOGEN FOOD SAFETY US HOLDCO CORPORATION, Lansing, MI (US)

(72) Inventors: Evan D. Brutinel, Inver Grove Heights, MN (US); Kurt J. Halverson, Lake Elmo, MN (US)

(73) Assignee: NEOGEN FOOD SAFETY US HOLDCO CORPORATION, Lansing, MI (US)

( * ) Notice: Subject to any disclaimer, the term of this patent is extended or adjusted under 35 U.S.C. 154(b) by 955 days.

(21) Appl. No.: 17/011,259

(22) Filed: Sep. 3, 2020

(65) Prior Publication Data

US 2020/0399674 A1 Dec. 24, 2020

Related U.S. Application Data

(62) Division of application No. 15/503,496, filed as application No. PCT/US2015/045786 on Aug. 19, 2015, now abandoned.

(Continued)

(51) Int. Cl.
*B01L 3/00* (2006.01)
*B01F 23/00* (2022.01)
(Continued)

(52) U.S. Cl.
CPC ............... *C12Q 1/06* (2013.01); *C12M 23/34* (2013.01); *C12M 23/38* (2013.01); *C12M 25/06* (2013.01);
(Continued)

(58) Field of Classification Search
CPC ............ C12Q 1/06; C12Q 1/04; C12M 23/34; C12M 23/38; C12M 25/06; C12M 37/04; C12M 41/36
See application file for complete search history.

(56) References Cited

U.S. PATENT DOCUMENTS 3,338,794 A   8/1967   Bladel
4,425,268 A   1/1984   Cooper
(Continued)

FOREIGN PATENT DOCUMENTS

CN   102971433   3/2013
DE   37 32 142   4/1989
(Continued)

OTHER PUBLICATIONS

ASTM Designation: D5459-95 (reapproved 2012) entitled "Standard Test Method for Machine Direction Elastic Recovery and Permanent Deformation and Stress Retention of Stretch Wrap Film".
(Continued)

*Primary Examiner* — Jennifer Wecker
*Assistant Examiner* — Oyeleye Alexander Alabi
(74) *Attorney, Agent, or Firm* — Hylton-Rodic Law PLLC

(57) ABSTRACT

The present disclosure provides a device that includes a base comprising a substrate having a first major surface, a pressure sensitive adhesive adhered to at least a portion of the first major surface, a polymeric cover film coupled to the substrate via the adhesive, a plurality of isolated closed compartments disposed between the substrate and the cover film, and an aqueous liquid disposed in two or more of the closed compartments. The cover film is a composite film comprising ethylene vinyl acetate copolymer, a linear copolymer of ethylene and a higher alkene, and a tackifier. Each
(Continued)

compartment of the plurality is defined by a seal that prevents liquid communication with at least one other compartment of the plurality. Methods of using the device for partitioning a sample, for analyzing a sample, and for culturing a microorganism are also provided.

16 Claims, 8 Drawing Sheets

Related U.S. Application Data

(60) Provisional application No. 62/039,638, filed on Aug. 20, 2014.

(51) Int. Cl.

| | | |
|---|---|---|
| *B01F 23/41* | (2022.01) | |
| *B01F 101/23* | (2022.01) | |
| *B23Q 17/24* | (2006.01) | |
| *C12M 1/00* | (2006.01) | |
| *C12M 1/12* | (2006.01) | |
| *C12M 1/34* | (2006.01) | |
| *C12Q 1/04* | (2006.01) | |
| *C12Q 1/06* | (2006.01) | |
| *C12Q 1/18* | (2006.01) | |
| *G01N 21/3577* | (2014.01) | |
| *G01N 21/359* | (2014.01) | |
| *G01N 21/39* | (2006.01) | |
| *G01N 21/45* | (2006.01) | |
| *G01N 21/64* | (2006.01) | |
| *G01N 33/50* | (2006.01) | |
| *G01N 33/68* | (2006.01) | |

(52) U.S. Cl.
CPC ............ *C12M 37/04* (2013.01); *C12M 41/36* (2013.01); *C12Q 1/04* (2013.01)

(56) References Cited

U.S. PATENT DOCUMENTS

| | | | |
|---|---|---|---|
| 4,775,626 A | 10/1988 | Armenta | |
| 5,116,748 A | 5/1992 | Takahashi | |
| 5,461,234 A | 10/1995 | Miyazaki et al. | |
| 5,518,892 A | 5/1996 | Naqui et al. | |
| 5,620,895 A * | 4/1997 | Naqui .................... | C12Q 1/04 |
| | | | 435/304.2 |
| 5,700,655 A | 12/1997 | Croteau et al. | |
| 6,007,914 A | 12/1999 | Joseph et al. | |
| 6,322,750 B1 | 11/2001 | Barclay | |
| 6,391,578 B2 | 5/2002 | Williams et al. | |
| 6,458,533 B1 | 10/2002 | Felder et al. | |
| 6,627,159 B1 | 9/2003 | Bedingham et al. | |
| 6,649,406 B1 | 11/2003 | Williams | |
| 6,696,286 B1 | 2/2004 | Halverson et al. | |
| 6,908,746 B2 | 6/2005 | Lorentzen et al. | |
| 7,582,472 B2 | 9/2009 | Smith et al. | |
| 7,811,783 B2 | 10/2010 | Lorentzen et al. | |
| 8,753,834 B2 | 6/2014 | Miller et al. | |
| 2001/0024805 A1 | 9/2001 | Williams et al. | |
| 2003/0175510 A1 | 9/2003 | Sherman et al. | |
| 2005/0239200 A1* | 10/2005 | Beckwith ............... | C12M 41/34 |
| | | | 435/299.1 |
| 2006/0073470 A1* | 4/2006 | Noda ..................... | C12Q 1/04 |
| | | | 435/4 |
| 2010/0137163 A1 | 6/2010 | Link et al. | |
| 2011/0250597 A1 | 10/2011 | Larson et al. | |
| 2021/0196642 A1 | 7/2021 | Cade et al. | |

FOREIGN PATENT DOCUMENTS

| | | | | |
|---|---|---|---|---|
| JP | S57-074094 | | 5/1982 | |
| JP | H048298 | A | 1/1992 | |
| JP | 2008-029332 | | 2/2008 | |
| JP | 2013202032 | | 10/2013 | |
| RU | 2 408 734 | | 1/2011 | |
| WO | WO 1995/23026 | | 8/1995 | |
| WO | WO 1996/34028 | | 10/1996 | |
| WO | WO 1996/34029 | | 10/1996 | |
| WO | WO 1996/35458 | | 11/1996 | |
| WO | WO-1999006589 A1 * | | 2/1999 | |
| WO | WO 99/29831 | | 6/1999 | |
| WO | WO-1999032601 A1 * | | 7/1999 | ........... B01L 3/5085 |
| WO | WO 2000/03035 | | 1/2000 | |
| WO | WO 2000/37683 | | 6/2000 | |
| WO | WO 2002/01181 | | 1/2002 | |
| WO | WO 2005/021157 | | 3/2005 | |
| WO | WO 2005/108545 | | 11/2005 | |
| WO | WO 2008/006848 A | | 1/2008 | |
| WO | WO 2011/073998 A | | 6/2011 | |
| WO | WO 2011/151793 | | 12/2011 | |
| WO | WO 2012012106 | | 1/2012 | |
| WO | WO 2013/063230 | | 5/2013 | |

OTHER PUBLICATIONS

Dunfield, E.M. et al.; "Simple and rapid fabrication of paper microfluidic devices utilizing Parafilm®"; Chips and Tips (published on-line by the Royal Society of Chemistry); 2012; 3 pgs.

Harada, et al. "Bacterial flora analysis of sulfate-reducing bacteria under a slightly aerobic condition," Summary of the SCEJ 12th Students Meeting (Fukuoka Convention), 2010, p. 111, M06.

Juneja et al. 1997. Journal of Food Protection. 30(10):1163-1166. "Thermal Destruction of *Escherichia coli* O157:H7 in Hamburger".

Takeuchi, et al., "Methods for the Determination of the Number and the Activity of Sulfate-Reducing Bacteria, Japan Journal of Water Pollution Research," 1988 vol. 11, Issue 1, pp. 38-49.

Tittsler ("Advantages of Peptone Iron Agar for the Routine Detection of Hydrogen Sulphide Production") American Journal of Public Health, vol. 27, 1240-1242, 1937).

* cited by examiner

DEVICES AND METHODS FOR SAMPLE PARTITIONING AND ANALYSIS

CROSS REFERENCE TO RELATED APPLICATIONS

This application is a divisional of U.S. patent application Ser. No. 15/503,496, filed Feb. 13, 2017, which is a national stage filing under 35 U.S.C. 371 of PCT/US2015/045786, filed Aug. 19, 2015, which claims the benefit of U.S. Provisional Patent Application No. 62/039,638, filed Aug. 20, 2014, the disclosures of which are incorporated by reference in their entireties herein.

TECHNICAL FIELD

The invention relates to a method of analyzing, for instance, enumerating and/or detection of microorganisms or other biological material in a liquid sample and a device adapted for use in such a method.

BACKGROUND

Many industries need to detect and quantify biological material in a sample, for instance, the determination of microbial concentration in food and water is an essential part of food and water quality testing. Similar demands arise from a multitude of industries including food, biotechnological, pharmaceutical, water treating industry, and also in medical microbiological diagnostics, environmental and scientific research. Samples are commonly scrutinized to, for instance, monitor microbial population in a production environment, in-process controls, post storage and also final product testing.

Classical methods for the examination of samples particularly liquid samples typically demands incubation time or reaction time for analysis. Analysis may involve several different kinds of chemical, biochemical, physical or optical techniques and require many hours or even days for incubation and subsequent analysis. Reducing the time for quantitative and qualitative analysis of samples is very essential for making rapid decisions in quality and process control operations.

With regard to testing of aqueous biological samples, it is advantageous to partition the sample into aliquots so that the desired reaction or growth occurs and can be detected much more rapidly than the same reaction or growth in the original larger volume. Biological samples such as microbiological samples and molecular biology samples would often require such partitioning, in order to be analyzed precisely qualitatively and/or quantitatively.

Such methods and device envisage a series of tiny compartments which are filled en masse with an aqueous sample. In each case, once filled and sealed, the desired reaction or growth occurs and can be detected much more rapidly than the same reaction or growth in the original larger volume.

SUMMARY

In general, the present disclosure relates to devices and method for partitioning a liquid sample (e.g., an aqueous liquid sample). In addition, the present disclosure relates to a method of using the devices to detect a microorganism and/or biomolecule in the liquid sample.

In one aspect, the present disclosure provides a quick, simple and convenient device for partitioning of liquid sample into a large number of smaller discrete volumes in an efficient, robust and economical manner.

The present disclosure further provides a pouch that can be used for partitioning of liquid sample into a large number of smaller discrete volumes in an efficient, robust and economical manner. Advantageously, the pouch may be provided with nutrients and/or indicators disposed therein for detecting microorganisms. The nutrients and/or indicators may be provided as a dry powder coating, which is dissolved when a liquid (e.g., an aqueous liquid) is dispensed into the pouch. The pouch can be used in a method to create a device in which the liquid is partitioned into a plurality of isolated, closed compartments.

Advantageously, the present disclosure provides a device for easy partitioning of liquid wherein the device comprises two films, one coated with a pressure sensitive adhesive and the other being deformable so as to conform to the shape of the desired partitions such that the sample is partitioned into small discrete units without permitting the mixing of sample in the adjacent compartments.

In one aspect, the present disclosure provides a device that can comprise a base comprising a substrate having a first major surface, a pressure sensitive adhesive adhered to at least a portion of the first major surface, a polymeric cover film coupled to the substrate via the adhesive, a plurality of closed compartments disposed between the substrate and the cover film, and an aqueous liquid disposed in two or more of the closed compartments. The cover film can be a composite film comprising a polymer and a tackifier. The composite film can comprise ethylene vinyl acetate copolymer, a linear copolymer of ethylene and a higher alkene, and the tackifier. Each compartment of the plurality can be defined by a seal that prevents liquid communication with another compartment of the plurality. The seal is formed by contact between the cover film and the pressure sensitive adhesive.

In another aspect, the present disclosure provides a device that can comprise a base comprising a substrate having a first major surface, a pressure sensitive adhesive adhered to at least a portion of the first major surface, a cover film coupled to the substrate via the adhesive, a plurality of closed compartments disposed between the substrate and the cover film, and an aqueous liquid disposed in two or more of the closed compartments. The cover film can have an elastic recovery of less than or equal to 20%. Each compartment of the plurality can be defined by a seal that prevents liquid communication with another compartment of the plurality. The seal is formed by contact between the cover film and the pressure sensitive adhesive.

The device as disclosed in the present invention finds a variety of applications in molecular biology, biochemistry, biotechnology and microbiology applications.

Advantageously, the device of the present invention facilitates improved time-to-result and easily expanded testing capabilities including rapid detection of microorganisms, molecular characterization, indicator organism testing, single organism pathogen enrichment, most probable number (MPN) style testing formats, and high-throughput post-enrichment biochemical characterization coupled with a easy-to-use and time saving benefit.

In yet another aspect, the present disclosure provides a method for partitioning liquid. The method can comprise depositing a predefined volume of liquid between a substrate and a polymeric cover film wherein said substrate is coated with water-insoluble pressure sensitive adhesive, and urging an external means against the cover film to bring discrete regions of the cover film in contact with the pressure sensitive adhesive of the substrate resulting in the partitioning of the liquid into a plurality of closed compartments disposed between the substrate and the cover film. The cover film can be a composite film comprising a polymer and a tackifier. The composite film can comprise ethylene vinyl acetate copolymer, a linear copolymer of ethylene and a higher alkene, and the tackifier.

In yet another aspect, the present disclosure provides a method for partitioning liquid. The method can comprise depositing a predefined volume of liquid onto a first surface of a substrate such that the liquid sample is disposed between the first surface and a polymeric cover film wherein said first surface is coated with water-insoluble pressure sensitive adhesive, and urging an external means against the cover film to bring discrete regions of the cover film in contact with the pressure sensitive adhesive of the substrate resulting in the partitioning of the liquid into a plurality of closed compartments disposed between the substrate and the cover film. The cover film can have an elastic recovery of less than or equal to 20%.

According to another aspect, the present disclosure provides a method for analyzing a liquid sample for its quantitative and qualitative aspects. The method can comprise depositing a liquid sample onto a first surface of a substrate such that the liquid sample is disposed between the first surface and a polymeric cover film wherein said first surface is coated with water-insoluble pressure sensitive adhesive, urging an external means against the cover film to bring discrete regions of the cover film in contact with the pressure sensitive adhesive of the substrate resulting in the partitioning of the liquid into a plurality of closed compartments disposed between the substrate and the cover film, and conducting a quantitative analysis or a qualitative analysis of at least one closed compartment of the plurality. The cover film can be a composite film comprising a polymer and a tackifier. The composite film can comprise ethylene vinyl acetate copolymer, a linear copolymer of ethylene and a higher alkene, and the tackifier.

According to another aspect, the present disclosure provides a method for analyzing a liquid sample for its quantitative and qualitative aspects. The method can comprise depositing a liquid sample onto a first surface of a substrate such that the liquid sample is disposed between the first surface and a polymeric cover film wherein said first surface is coated with water-insoluble pressure sensitive adhesive, urging an external means against the cover film to bring discrete regions of the cover film in contact with the pressure sensitive adhesive of the substrate resulting in the partitioning of the liquid into a plurality of closed compartments disposed between the substrate and the cover film, and conducting a quantitative analysis or a qualitative analysis of at least one closed compartment of the plurality. The cover film can have an elastic recovery of less than or equal to 20%.

In another embodiment, the present disclosure provides a method for the isolation, detection, culturing and enrichment of microorganisms, including anaerobic and aerobic forms.

In any embodiment, the analysis for the detection and enumeration of microorganisms is carried out by the approaches described herein which allow for the use of water-soluble indicator species, and reduces or eliminate the need for the several dilutions typically required in current microbiological analyses.

In yet another aspect, the present disclosure provides a method for culturing an aerobic or an anaerobic microorganism. The method can comprise mixing a sample with a liquid nutrient medium to render it liquefied, depositing the liquefied sample onto a first surface of a substrate such that the liquid sample is disposed between the first surface and a polymeric cover film wherein said substrate is coated with water-insoluble pressure sensitive adhesive, urging an external means against the cover film to bring discrete regions of the cover film in contact with the pressure sensitive adhesive of the substrate resulting in the partitioning of the liquid into a plurality of closed compartments disposed between the substrate and the cover film, and incubating the liquefied and partitioned sample, under conditions to facilitate at least one cell division of said microorganism. The cover film can be a composite film comprising a polymer and a tackifier. The composite film can comprise ethylene vinyl acetate copolymer, a linear copolymer of ethylene and a higher alkene, and the tackifier.

In yet another aspect, the present disclosure provides a method for culturing an aerobic or an anaerobic microorganism. The method can comprise mixing a sample with a liquid nutrient medium to render it liquefied, depositing the liquefied sample onto a first surface of a substrate such that the liquid sample is disposed between the first surface and a polymeric cover film wherein said first surface is coated with water-insoluble pressure sensitive adhesive, urging an external means against the cover film to bring discrete regions of the cover film in contact with the pressure sensitive adhesive of the substrate resulting in the partitioning of the liquid into a plurality of closed compartments disposed between the substrate and the cover film, and incubating the liquefied and partitioned sample, under conditions to facilitate at least one cell division of said microorganism. The cover film can have an elastic recovery of less than or equal to 20%.

Another aspect of the present invention is to provide a kit for partitioning a liquid sample into a plurality of discrete compartments. The kit can comprises a substrate having a first major surface with a layer of a water-insoluble pressure sensitive adhesive adhered thereto; and a composite cover film. The composite film can comprise ethylene vinyl acetate copolymer, a linear copolymer of ethylene and a higher alkene, and a tackifier.

Another aspect of the present invention is to provide a kit for partitioning a liquid sample into a plurality of discrete compartments. The kit can comprises a substrate having a first major surface with a layer of a water-insoluble pressure sensitive adhesive adhered thereto; and a polymeric cover film having an elastic recovery of less than or equal to 20%.

In any of the above embodiments of the kit, the substrate and/or the cover film can be substantially planar. In any of the above embodiments of the kit, the pressure sensitive adhesive can comprise silicone polyurea. In any of the above embodiments of the kit, the substrate further can comprise a secondary coating disposed on at least a portion of the adhesive. In any of the above embodiments of the kit, wherein a spacer element is coupled to the first major surface of the substrate. In any of the above embodiments of the kit, the cover film is attached to the substrate; wherein the spacer element, if present, is disposed between the substrate and the cover film.

In yet another aspect, the present disclosure provides a kit. The kit can comprise a substrate having a first major surface with a layer of a water-insoluble pressure sensitive adhesive adhered thereto, and a composite polymeric film. The polymeric film can comprise ethylene vinyl acetate copolymer, a linear copolymer of ethylene and a higher alkene, and a tackifier. The tackifier can be selected from a group consisting of a low molecular weight polyisobutene, polyterpenes, amorphous polypropylene, and microcrystalline wax.

In any embodiment of the kit, the composite polymeric film has an elastic recovery of less than or equal to 20%.

In yet another aspect, the present disclosure provides a kit. The kit can comprise a substrate having a first major surface with a layer of water-insoluble pressure sensitive adhesive adhered thereto, and a polymeric film having an elastic recovery of less than or equal to 20%.

In any of the above embodiments of the kit, the substrate and/or the polymeric film is substantially planar. In any of the above embodiments of the kit, the substrate and/or the polymeric film is substantially flat. In any of the above embodiments of the kit, the pressure sensitive adhesive comprises silicone polyurea. In any of the above embodiments of the kit, the substrate further comprises a secondary coating disposed on at least a portion of the adhesive. In any of the above embodiments of the kit, the secondary coating comprises a powdered nutrient and/or a plurality of glass bubbles. In any of the above embodiments of the kit, the secondary coating is substantially water-free. In any of the above embodiments of the kit, a spacer element is coupled to the first major surface of the substrate, as described hereinabove. In any of the above embodiments of the kit, the composite polymeric film is attached to the substrate, wherein the spacer element, if present, is disposed between the substrate and the cover film.

As described herein, the present invention has several advantages. First, the articles and methods eliminate the use of device having preformed compartments, thereby permitting the operator to choose from a variety of potential partition configurations (e.g., the number of compartments, the volume of each compartment, the total volume of sample) at the point of use. Second, use of microvolumes in microcompartments allows for a surprisingly rapid detection and enumeration of microorganisms in a liquid test sample. The invention is particularly useful in MPN analysis of a liquid test sample for a particular microorganism, such as *E. coli* or *S. aureus*. The invention allows MPN analysis to be conducted conveniently in a single device, as opposed to separate tubes, and advantageously requires a substantively shorter incubation time to reach detectable microorganism growth. Third, the use of microvolumes in microcompartments allows for the separation of a liquid test sample into a relatively larger number of test volumes. In general, the use of microvolumes in microcompartments provides a far greater number of runs, or repetitions, of a test on the liquid sample. In the case of MPN analysis, use of microvolumes in microcompartments provides a greater number of data points from which the MPN can be calculated, thereby significantly narrowing the 95% confidence limits for a given MPN result. Fourth, separation of sample into a large number of test volumes allows a higher concentration of microorganisms to be enumerated, thereby reducing or eliminating sample dilutions. Fifth, this invention allows MPN analysis to be conducted in a single device having the indicators and/or nutrients directly coated thereon. Sixth, this invention permits a wide counting range when performing MPN analysis.

The foregoing has outlined some of the most pertinent objects of the invention. These objects should be construed to be merely illustrative of some of the more prominent features and applications of the intended invention. The invention includes other features and advantages which will be described or will become apparent from the following more detailed description of the embodiment.

The terms "comprises" and variations thereof do not have a limiting meaning where these terms appear in the description and claims.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

The foregoing summary, as well as the following detailed description of the invention will be better understood when read in conjunction with the appended drawings. For the purpose of assisting in the explanation of the invention, there are shown in the drawings embodiments which are presently preferred and considered illustrative. It should be understood, however, that the invention is not limited to the precise arrangements and instrumentalities shown therein. In the drawings.

DETAILED DESCRIPTION

Figure 1A:
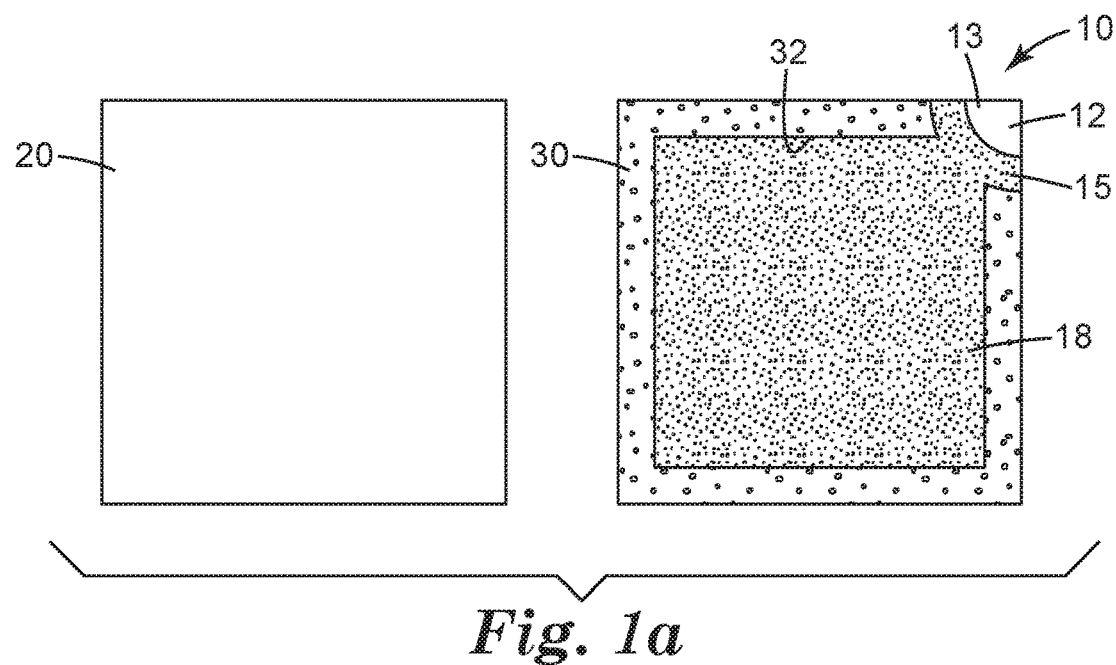
FIG. 1a is a plan view, partially in section, of one embodiment of the components of a device for detecting microorganisms according to the present disclosure.

The present invention will now be described more fully herein after. For the purposes of the following detailed description, it is to be understood that the invention may assume various alternative variations and step sequences, except where expressly specified to the contrary. Thus, before describing the present invention in detail, it is to be understood that this invention is not limited to particularly exemplified systems or embodiments that may of course, vary. The use of examples anywhere in this specification including examples of any terms discussed herein is illustrative only, and in no way limits the scope and meaning of the invention or of any exemplified term. Likewise, the invention is not limited to various embodiments given in this specification.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the device, to indicate or imply necessary or required orientations of the device, or to specify how the invention described herein will be used, mounted, displayed, or positioned in use.

As used herein, the singular forms "a," "an," and "the" include plural reference unless the context clearly dictates otherwise. The term "and/or" means one or all of the listed elements or a combination of any two or more of the listed elements.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

When the term "about" is used in describing a value or an endpoint of a range, the disclosure should be understood to include both the specific value and end-point referred to.

As used herein the terms "comprises", "comprising", "includes", "including", "containing", "characterized by", "having" or any other variation thereof, are intended to cover a non-exclusive inclusion.

The term "planar" as used herein refers to a plane involving two dimensions.

The expression "substantially planar" as used herein refers to a two dimensional surface. The material of the "substantially planar substrate" of the present invention (before forming the compartments) does not have three dimensional structure that define the ultimate shape, size, or volume of the claimed compartments.

The term "pressure sensitive adhesive" as used herein refers to an adhesive which upon application of pressure results in an adhesion with the adherend. No solvent, water, or heat is required to bring about adhesion. As the name "pressure-sensitive" indicates, the degree of bond is influenced by the amount of pressure applied.

The term "hydrophobicity" as used herein refers to the physical property of a molecule possessing relatively little or no affinity for water or aqueous media. Hydrophobic molecules tend to be non-polar and, thus, prefer other neutral molecules and non-polar solvents.

Hydrophobic molecules in water often cluster together, forming micelles. Water on hydrophobic surfaces will exhibit a high contact angle.

The term "elastomer" as used herein refers to any polymer with viscoelasticity (having both viscosity and elasticity) and very weak inter-molecular forces, generally having low Young's modulus and high failure strain compared with other materials. Each of the monomers which link to form the polymer is usually made of carbon, hydrogen, oxygen and/or silicon. Elastomers are amorphous polymers existing above their glass transition temperature, so that considerable segmental motion is possible. The term "elastic recovery" as used herein refers to the proportion of recovery after deformation and is quantified as percent recovery after elongation. The elastic recovery is measured by the percentage to which a polymer will recover its original length after initial elastic deformation. The higher the percentage of elastic recovery, the greater is the tendency of the polymer to recover to its original dimensions after initial deformation.

The term "closed compartment" as used herein refers to a defined and distinct space which retains the contents of each compartment in isolation without getting mixed with the contents of the adjacent compartment. The expression "plurality of closed compartments" as used herein refers to more than one such closed compartment being disposed between the substrate and cover film of the device as per the present invention.

The term "seal" as used herein refers to junction between the polymeric cover film and the substrate. This junction forms the compartments and prevents leakage, prevents mixing between compartments (e.g., adjacent compartments), and/or prevents contamination from the external environment.

The term "tackifier" as used herein refers to chemical compounds used in formulating adhesives to increase the tack, the stickiness of the surface of the adhesive. They are usually low-molecular weight compounds with high glass transition temperature. At low strain rate, they provide higher stress compliance, and become stiffer at higher strain rates.

The term "melt index" as used herein is a common measurement used to characterize thermoplastic polymers. It is an indirect, and inversely proportional, measure of the viscosity of the polymer when molten. One measures the mass of polymer melt which will flow through an orifice in a given amount of time under defined conditions of temperature, pressure, and geometry. The larger the melt index value, the lower is its viscosity, and therefore, the average molecular weight of the polymer is lower. Higher molecular weight polymers will be more viscous and less will flow under the same conditions so the melt index will be a smaller number. The melt index is typically expressed in terms of grams of polymer which flow out in a ten minute period, thus g/10 min or dg/min.

The term "specific gravity" as used herein refers to the ratio of the density of a substance to the density (mass of the same unit volume) of a reference substance.

The term "optical transmittance" or "clarity" refers to the optical distinctness with which an object can be seen when viewed through plastic film, sheet, glass, etc. Clarity depends upon the linearity of the passage of light rays through the material and is determined by small-angle scattering. It is the regular transmittance of a material which is measured by a photoelectric detector by determining the percent of light transmitted through the material.

The term 'liquid sample' as used herein refers to any sample in the liquid state or may be dissolved in a liquid to form the liquefied sample or a sample which has been liquefied.

The term "sample" may be any biological sample or environmental sample such as waste water, food, a surface swab, or swabs from other surfaces, such as a throat, or other samples well known to those in the art. This sample may be a liquid sample, or may be dissolved in a liquid to form the liquefied sample. As noted above, the biological material that can be detected is any material that forms a discrete particle, such as a microorganism, which may be quantified by determining the presence or absence of such a biological material within each well of the incubation plate.

The term "anaerobic microorganism" or "anaerobe" as used herein refers to microorganisms which are sensitive to oxygen and will not grow in the presence of oxygen. An anaerobic microorganism or anaerobe is any organism that does not require oxygen for growth. Anaerobic microorganisms include both obligate anaerobes and facultative anaerobes. Obligate anaerobes are those microorganisms which will die when exposed to atmospheric levels of oxygen. A facultative anaerobe is an organism that can carry out aerobic respiration if oxygen is present, but is capable of switching to fermentation or anaerobic respiration if oxygen is absent. Methods and systems of the present invention could be used for the enrichment and detection of both obligate anaerobes and facultative anaerobes.

The term "culture" or "growth" of microorganisms as used herein refers to the method of increasing the number of microbial organisms by letting them reproduce in predetermined culture media under conditions conducive for their growth. More particularly it is the method of providing a suitable culture medium and conditions to facilitate at least one cell division of a microorganism. Culture media are solid, semisolid or liquid media containing all of the nutrients are required for physical growth parameters essential for microbial growth.

Assemblies, devices, and methods of the present disclosure can be used to parturition a liquid sample and, optionally, analyze the sample for the present or absence of biomolecules and/or microorganisms. The assemblies, devices, and methods are particularly useful in Most Probable Number (MPN) methods of analyzing a sample for the presence and quantity of microorganisms.

The most probable number method is described in International Publication No. WO95/23026, which is incorporated herein by reference in its entirety. In this method, a volume of water sample is dispensed into several tubes (e.g., 10×10; 10 tubes each containing 10 ml) and bacteria in each tube allowed to grow. After incubation at a specific temperature for a specific time, the number of positive tubes is counted. The most probable number in these embodiments can be determined from Formula I:

$$\text{MPN}/100 \text{ ml} = (P \times 100)/(NT)^{1/2} \quad \text{(Formula I)}$$

where P is the number of positive tubes, N is the volume (ml) of sample in negative tubes, T is the volume (ml) sample in all tubes, and MPN is the most probable number. A major drawback of the method is the range of 95% confidence limits is large, when only a few tubes are used. Such confidence limits are calculated roughly using Formula II:

$$\text{Log(MPN)} \pm 1.96(0.58/n^{1/2}) \quad \text{(Formula II)}$$

where n is the number of tests.

All of the current devices/methods in the art suffer from the problem of how to efficiently fill tiny compartments in a simple manner. Current solutions include using devices with pre-formed compartments, applying a vacuum, centrifugation, and even the formation of micro drops in an oil emulsion. In each case, the method required to partition the liquid is cumbersome and real-world samples containing particulates such as food are incompatible. Because the conventionally known methods are inadequate for routine use where rapid and easy processing of numerous and varied samples, there is need for an improved method and device.

The present invention solves the problems associated with currently used systems for partitioning small volumes of liquid sample into a large number of smaller discrete volumes. In general, the present invention provides a device and method to effect rapid and accurate detection and enumeration of microorganisms based on the surprising result that the use of microvolumes substantially increases the speed of detection. Microorganisms are detected and/or enumerated not only when whole cells are detected directly, but also when such cells are detected indirectly, such as through detection or quantization of cell fragments, cell components, cell-derived biological molecules, or cell by-products.

Automated detection and enumeration of colonies on both standard agar plates, as well as PETRIFILM™ plates, is difficult and suffers from a number of limitations. The position of each well in the stamped plates however is fixed, and would not require an identification algorithm. An automated detection platform would simply need to measure the fluorescence in a given area and determine if it is above a set threshold. Customers that do not require the fastest possible time-to-result would be able to observe (and enumerate) positive compartments using ambient light or a simple hand-held illumination source (e.g., black light), thereby obviating the need for an auto-reader. When a sample is partitioned into many smaller samples the effective concentration of a microorganism or other biomolecules like viruses, nucleotides, metabolites etc., that ends up in any given partition is increased by orders of magnitude, increasing the speed of reaction chemistries and reducing the time to detection.

The device of the present invention has another significant advantage over the known solid culture techniques. Advantageously, the method of the present invention is less labor-intensive, allows better distribution of sample, and provides a more accurate estimate of microbial concentration. This is because the correspondingly larger number of sample aliquots in the compartments provides a correspondingly narrower confidence limit interval.

The present invention has manifold applications in various fields that require qualitative and quantitative analysis of micro volumes of liquid samples. The field of applications may include without limitation microbiology, molecular biology, biotechnology, chemistry and the like.

Exemplary microbiological applications of the qualitative and quantitative analyses include without limitation, growth assessment, monitoring, single cell enrichment cultures, isolation, performance of secondary tests that are not compatible with growth, most probable number (MPN) style testing using compartments of different sizes.

Non-limiting exemplary molecular biological applications include polymerase chain reaction assays, detection and quantification of biomolecules like nucleotides, amino acids, peptides, proteins, metabolites and the like.

With reference to the Figures, a device of the present invention is constructed as described in detail below.

Figure 1B:
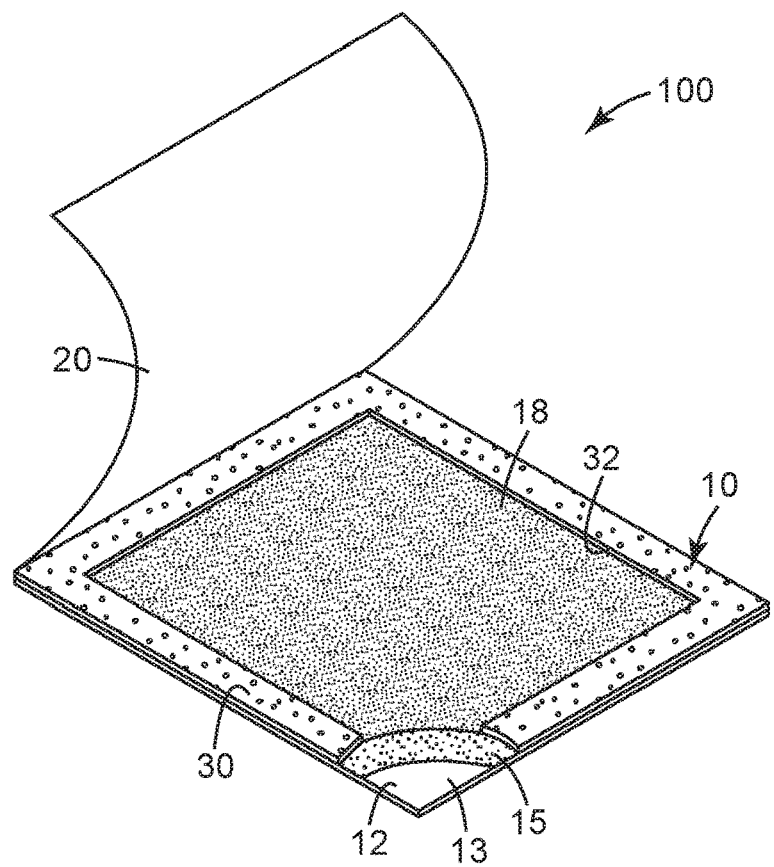
FIG. 1b is a perspective view of an assembly comprising the components of FIG. 1a, the assembly having the cover film in an open position for inoculating the assembly.
Figure 1C:
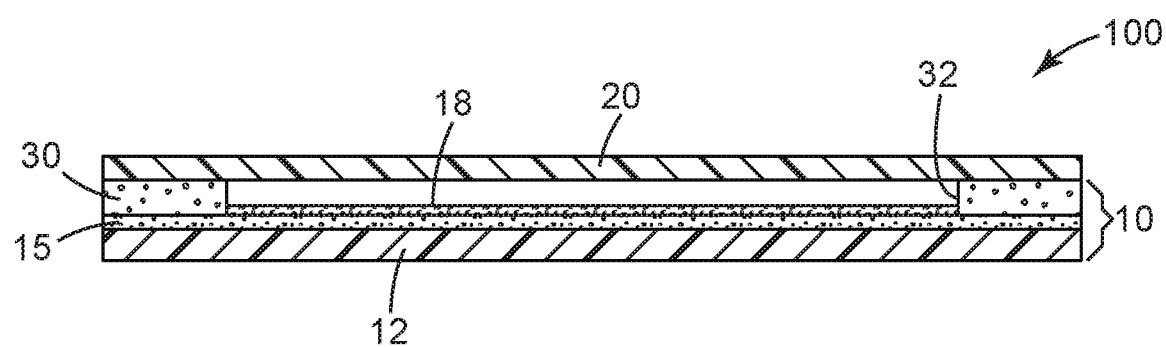
FIG. 1c is a cross-sectional side view of the assembly of FIG. 1B, the assembly having the cover film in a closed position.

As shown in FIGS. 1a-1c, a device of the present disclosure can be made from components that include a base 10 and a cover film 20. The base comprises a substrate 12. In any embodiment, the substrate 12 having a first surface 13 that is substantially planar. In any embodiment, the substrate 12 can be thin (e.g., less than 5 mm thick) and substantially flat (i.e., sheet-like). In any embodiment, the substrate 12 may be self-supporting. Optionally, the substrate 12 may be optically translucent or transparent. Preferably, the substrate 12 is water insoluble or has a water-insoluble coating (not shown) on at least a portion of the first surface 13. Preferably, the substrate 12 will not leach any chemicals (e.g., chemicals that may inhibit microorganism growth and/or activity (e.g., an enzyme activity used to detect the microorganism)) upon contact with an aqueous liquid (e.g., an aqueous sample).

In any embodiment, the base 10 and cover film 20 can be assembled into an assembly 100 as shown in FIG. 1b. The cover film 20 may be attached to the substrate 10 and/or spacer element 30 via a suitable attachment means (e.g., a pressure-sensitive adhesive, not shown). Advantageously, a liquid sample (not shown) can be deposited into the assembly 100 simply by lifting the cover film 20 to expose the area (e.g., defined by spacer element 30 surrounding the adhesive 15 and secondary coating 18 (described below) of the illustrated embodiment) onto which the sample is to be deposited.

The substrate 12 can be fabricated, for example, from polymeric films or other appropriate materials. Appropriate polymers include without limitation polyethylene, polypropylene, polyester, polyimides, fluoropolymers, polycarbonates, polyurethanes, polystyrenes, derivatives thereof, and combinations thereof. Other appropriate materials may include without limitation metal foils like aluminum foils, copper foils, steel foils, laminated foils, paper foils, and paper boards. In any embodiment, the substrate 12 is a biaxially oriented polypropylene.

The substrate 12 has a thickness of at least about 0.01 mm. In any embodiment, the substrate 12 has a thickness greater than 5 mm, less than or equal to 5 mm, less than or equal to about 2 mm, less than or equal to about 1 mm. Preferably, the substrate 12 does not exhibit substantial light-absorbing properties (e.g., in the u.v. and/or visible wavelengths) that would interfere with any fluorescent or color-based indicator system that may be employed for the purposes of detection.

In any embodiment, the substrate may be optically transmissible with respect to visible wavelengths, ultraviolet wavelengths, and/or infrared wavelengths of electromagnetic radiation.

Referring back to FIGS. 1a-1c, at least a portion of the first major surface 13 has a water-insoluble pressure sensitive adhesive (PSA) layer 15 adhered thereto. When a device of the present disclosure is assembled as described herein, PSA layer 15 forms a bond with a cover film 20 when pressure is applied to the cover film 20 to bring it into contact with the PSA layer 15. No solvent, water, or heat is needed to activate the PSA adhesive and the degree of bond is influenced by the amount of pressure (and topology of the external means, described below) which is used to contact the adhesive 15 to the cover film 20. The PSAs of the present invention are able to retain their adhesive properties even in the presence of aqueous liquids and certain non-aqueous liquids that do not substantially interfere with the adhesive. The thickness of the PSA layer coated onto the substrate 12 is at least about 0.02 mm. In any embodiment the thickness of the PSA layer is in the range of about 0.02 mm to about 0.1 mm. Suitable PSAs include without limitation silicone polyurea adhesive and the like.

Suitable PSAs comprise an elastomer compounded with a suitable tackifier. The pressure-sensitive adhesive is substantially insoluble in aqueous liquids (e.g., water, aqueous culture media, aqueous buffers). Neither the elastomeric compound nor the tackifier should cause substantial inhibition of microorganism growth and/or activity. In any embodiment, the pressure-sensitive adhesive may be optically transmissible with respect to visible wavelengths, ultraviolet wavelengths, and/or infrared wavelengths of electromagnetic radiation.

Other suitable compositions may be based on the family of silicone-polyurea based pressure sensitive adhesives. Such compositions are described in the following documents, each of which is incorporated herein by reference in its entirety: U.S. Pat. No. 5,461,134 (Leir et al.); U.S. Pat. No. 6,007,914 (Joseph et al.); International Publication No. WO96/35458 (and its related U.S. patent application Ser. No. 08/427,788 (filed Apr. 25, 1995); Ser. No. 08/428,934 (filed Apr. 25, 1995); Ser. No. 08/588,157 (filed Jan. 17, 1996); and Ser. No. 08/588,159 (filed Jan. 17, 1996)); International Publication No. WO 96/34028 (and its related U.S. patent application Ser. No. 08/428,299 (filed Apr. 25, 1995); Ser. No. 08/428,936 (filed Apr. 25, 1995); Ser. No. 08/569,909 (filed Dec. 8, 1995); and Ser. No. 08/569,877 (filed Dec. 8, 1995)); and International Publication No. WO 96/34029 (and its related U.S. patent application Ser. No. 08/428,735 (filed Apr. 25, 1995) and Ser. No. 08/591,205 (filed Jan. 17, 1996)).

In any embodiment, the base 10 optionally comprises a spacer member 30 attached to the substrate 10. Optionally, the spacer member 30 may be adhered to the adhesive layer 15. The spacer member 30 comprises an aperture 32 that exposes a portion of PSA layer 15 that defines the perimeter of an area used to create compartments in a device of the present disclosure, as described hereinbelow.

Suitable materials for the spacer member 30 include, for example, any natural or synthetic substance which may be readily available in sheet form. Preferably, the spacer member 30 does not substantially inhibit microorganism growth or activity and does not absorb aqueous liquid (e.g., is constructed from or coated with hydrophobic materials). Polyethylene, polypropylene, polyethylene terephthalate and polystyrene are a few examples of suitable synthetic materials. In particular, relatively inexpensive commercially available polystyrene foams and polyethylene foams are preferred. Natural substances such as metal e.g. foil sheets, wood and the like, optionally coated with a hydrophobic coating, are less preferred alternatives.

The thickness of the spacer member 30 should be sufficient to create an interior volume in the device that is large enough to hold the desired sample volume. In any embodiment, the spacer member 30 can be less than 1 mm thick, at least about 0.02 mm thick, at least about 1 mm thick, at least about 1.5 mm thick, or at least about 2 mm thick.

In any embodiment of the present invention, the substrate coated with a primary coating of PSA (i.e., PSA layer 15) may further comprise a secondary coating. The optional secondary coating 18 may include without limitations one or more water-soluble reagents such as nutrients, dehydrated or powdered culture medium, selective agents (e.g., antibiotics, salts) chemicals, dyes, proteins, peptides, nucleotides, enzymes and antibodies, for example. Thus, when this type of secondary coating 18 is exposed to an aqueous liquid, the water-soluble reagent dissolves, thereby exposing the adhesive and permitting it to bond with the cover film 20 to form compartments as described herein.

Alternatively or additionally, the secondary coating 18 may comprise water-insoluble particles (e.g., hollow or solid glass microspheres, or fragments thereof) having a diameter that less than or equal to the thickness of the adhesive 15. With this type of secondary coating 18, the water-insoluble particles can be pushed, with or without breakage of the microspheres) into the adhesive layer 15 (e.g., by pressure applied through the cover film, thereby exposing the adhesive and causing the cover film to bond to the adhesive, as described hereinbelow. In any embodiment, pushing the microspheres into the adhesive layer may cause breakage of the microspheres. Advantageously, in any embodiment, the secondary coating 18 temporarily prevents adhesion of the cover film 20 to the adhesive layer 15 until a liquid is deposited into the assembly 100 thereby dissolving the secondary coating (if the secondary coating 18 comprises a water soluble reagent) and exposing the adhesive layer or until pressure is applied to the secondary coating (if the secondary coating 18 comprises water-insoluble particles) to expose the adhesive and thereby permit the adhesive to bond with the cover film 20.

In any embodiment, a secondary coating 18 of the present disclosure can be substantially water-free. As used in the specification and claims, the phrase "substantially water-free" designates a coating which has a water content no greater than about the water content of the dehydrated coating once it has been permitted to equilibrate with the ambient environment.

With reference to FIGS. 1a-1c, the cover film 20 can be fabricated from any elastic polymeric film material that is non-water absorbent (e.g., hydrophobic) and having an elastic recovery of no more than 20%. Elastic recovery of a plastic film can be measured, for example, using ASTM D5459-95(2012) "Standard Test Method for Machine Direction Elastic Recovery and Permanent Deformation and Stress Retention of Stretch Wrap Film"; ASTM International, West Conshohocken, PA; which is incorporated herein by reference in its entirety. The cover film 20 is preferably a self-sealing, moldable and flexible film such as, for example, the composite film available from Bemis Flexible Packaging Company (Oshkosh, WI) under the trade name PARAFILM®.

In any embodiment, the cover film may be optically transmissible with respect to visible wavelengths, ultraviolet wavelengths, and/or infrared wavelengths of electromagnetic radiation.

The cover film 20 can be fabricated, for example, from polymeric films or other appropriate materials. Suitable polymeric films are disclosed in U.S. Pat. No. 4,425,268, which is incorporated herein by reference in its entirety. The polymeric films may be appropriate composite of polymers and tackifiers. The appropriate polymers may include without limitation ethylene vinyl acetate copolymer, linear copolymer of ethylene and a higher alkene. The appropriate tackifier may include without limitation a low molecular weight polyisobutene, polyterpenes, amorphous polypropylene, and microcrystalline wax. Advantageously cover film 20 is fabricated using a composition of high molecular weight copolymer of ethylene and vinyl acetate and a linear copolymer of ethylene and a higher alkene.

The melt index of the high molecular weight copolymer is between about 0.1 to about 4.0. The specific gravity of the linear copolymer is between about 0.917 and about 0.945. In any embodiment, the cover film 20 has a thickness in the range of 0.02 mm to 0.5 mm, preferably in the range of 0.1 to 0.25 mm, more preferably in the range of 0.1 to 0.15 mm. Upon stretching of this cover film 20, the thickness of the layer may decrease to about 0.01 mm to 0.25 mm. This stretching of the cover film 20 resulting in decreased thickness of the film can contribute to efficient gaseous exchange between the sealed compartments and their external environment but does not allow moisture to pass through. The cover film 20 has low water permeability and is insensitive to moisture vapor. Advantageously, these properties of the cover film 20 and the device in general help in efficient culturing of aerobic and anaerobic microorganisms as illustrated in an embodiment of the present invention.

Figure 2A:
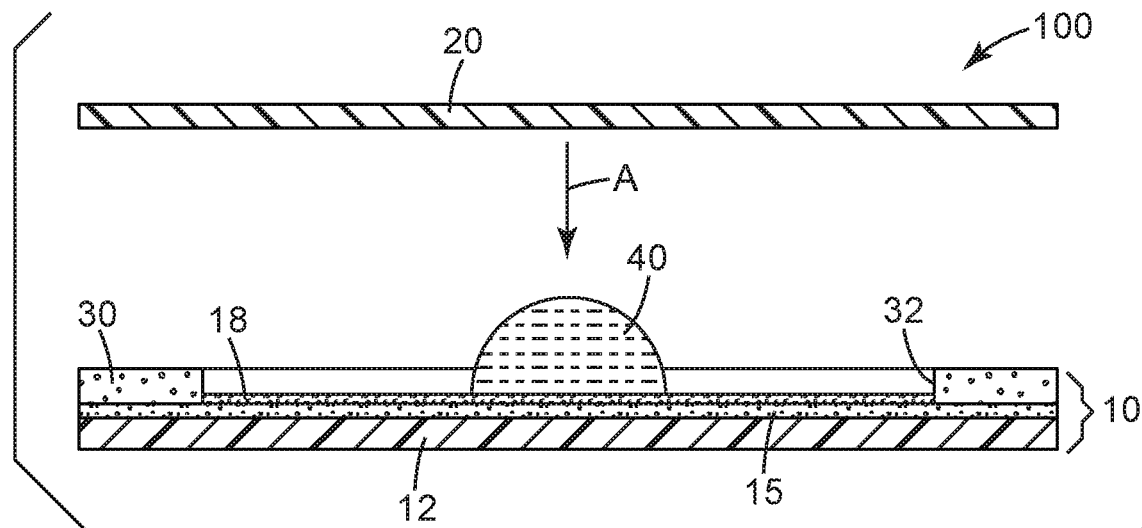
FIGS. 2a-d are various views showing one embodiment of the use of the components of FIG. 1a to partition a liquid sample and to produce a device comprising a spacer element according to the present disclosure.
Figure 2B:
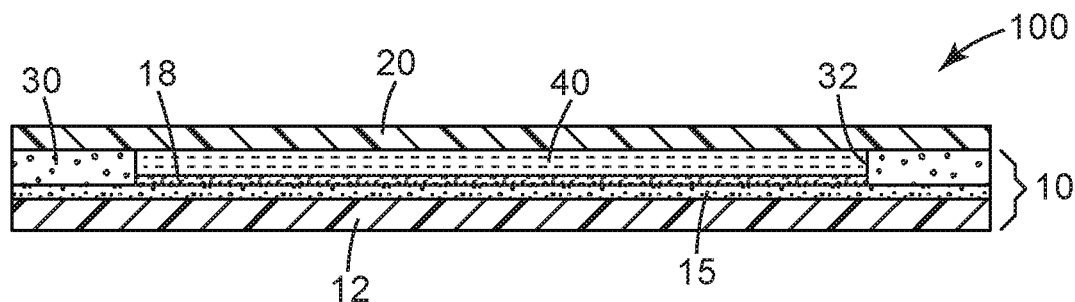

Returning to the drawings, FIGS. 2a-2d show one embodiment of a method of forming a detection device (e.g., detection device 1000 of FIG. 2d) according to the present disclosure. The detection device 1000 is formed from an assembly 100 (FIG. 2b) as described herein. With the cover film 20 at least partially separated from the base 10 (as shown in FIG. 2a), an aqueous sample 40 is applied (e.g., by pipet) to the base 10 of the assembly. The sample 40 is applied to the secondary coating 18, if present, or the pressure sensitive adhesive 15 within an area defined by the aperture 32 of the spacer member 30. The spacer member 30 functions to contain the sample 40 and prevent it from escaping or leaching out. Appropriate spacer members 30 for defining the sample area may include without limitation bumpers, spacers, rods and metallic rims. The liquid sample 40 is dispensed in the sample area and covered with a cover film 20 by bringing the cover film 20 into contact with the sample 40 and the base 10. A person having ordinary skill in the art will recognize a device of the present disclosure can be dimensioned to accommodate samples having various volumes. For example, the sample volume may be as small as about 50 µL or as large as about 100 mL or more. Preferably, the entire sample volume is distributed into the compartments of a device according to the present disclosure. If the secondary coating 18 is a water-soluble reagent, as disclosed herein, contact between the aqueous sample 40 and the secondary coating 18 will dissolve the coating, thereby placing the adhesive layer 15 in fluid communication with the sample 40, as shown in FIG. 2b.

As shown in FIG. 2b, urging the cover film 20 toward the base 10 (as shown by arrow "A" in FIG. 2a) spreads the sample 40 so as to fill the available volume in the base 10 defined by the substrate 12 and the spacer member 30. Placement of the cover film 20 against the base also expels substantially all of the air from the assembly 100. Efficient spreading of the liquid sample may be done in any number of ways using methods known in the art such as "rolling" the cover film (e.g., from one edge of the assembly 100 to the opposite edge) onto the spacer member 30; using spreading tools like rollers, metallic spreaders, polymeric spreaders, bent glass rods, or the like; tipping the device; or applying manual pressure to the cover film, for example.

Figure 2C:
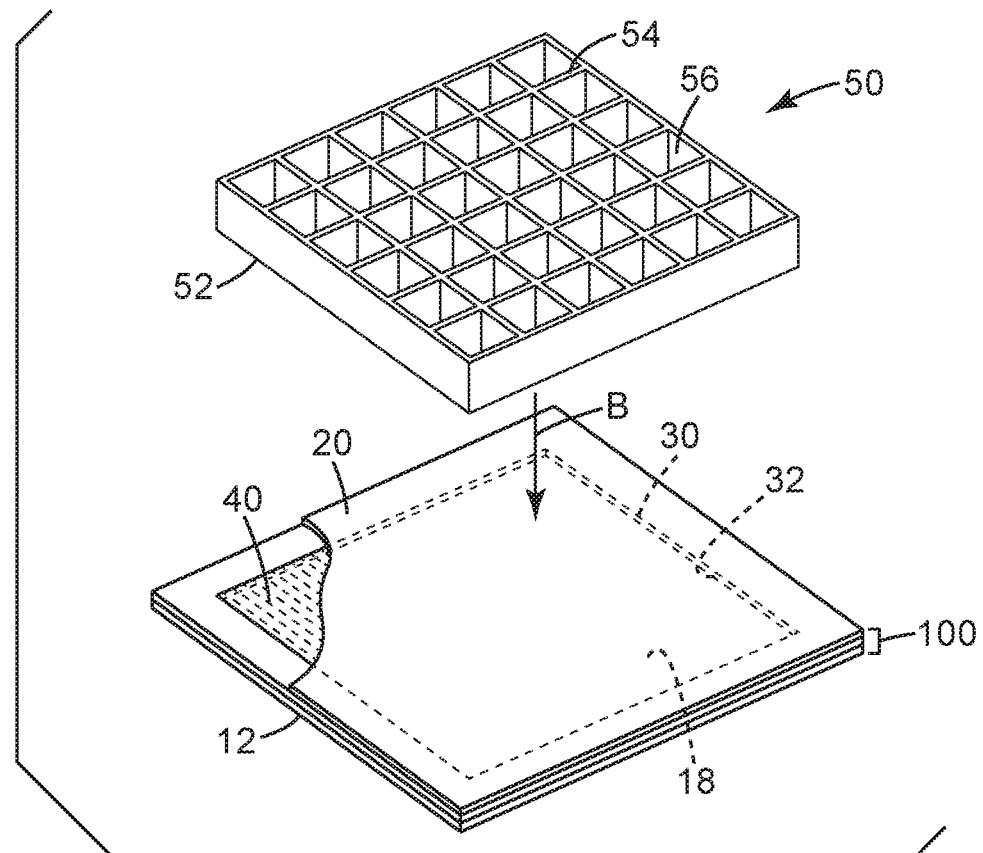
Figure 2D:
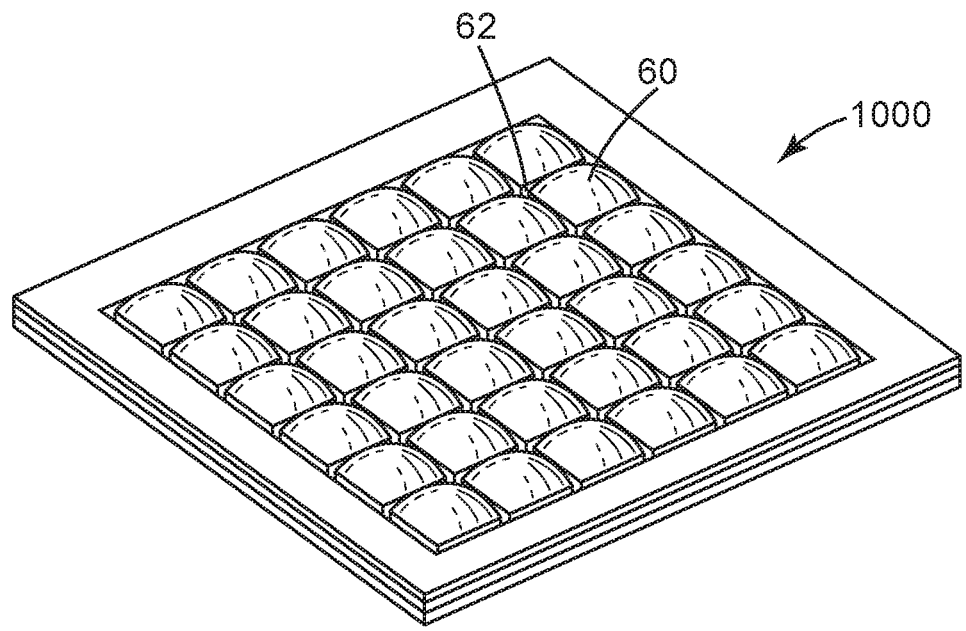

After assembling the base 10 and the cover film 20 to form the assembly 100 with the liquid sample 40 disposed therein, a plurality of compartments are formed to produce the detection device 1000 (FIG. 2d). In any embodiment, the compartments have a predetermined volume. In any embodiment, the volume of each compartment of the plurality of compartments is about equivalent to the volume in each of the other compartments. The sealing of the plurality of compartments at the point of contact between the cover film 10 and the pressure sensitive adhesive 15 coated on the substrate 12 is achieved by the application of pressure by external means to create a predefined pattern of seals where the cover film 20 contacts the adhesive layer 15 of the base 10. The hydrophobicity of the cover film 20 and/or the PSA layer 15 of the base 10 assists in preventing cross-contamination of the liquid confined in adjacent compartments.

The external means is employed for urging the cover film 20 to come in contact with the pressure sensitive adhesive 15 of the base 10 at specified areas. This is achieved using any tool or device (e.g., tool 50 of FIG. 2c) with the desired patterned surface (i.e., a surface having a predefined pattern of cavities) depending on the size, shape and number of compartments desired to be achieved. The tool 50 may be any patterned device (e.g., a 96-well or 384-well microtiter plate) possessing a plurality of predetermined ridges and cavities that can be used to form complementary-patterned structures on a moldable surface when the tool 50 is impressed thereupon. The size, shape, and therefore volume of the compartments formed in the process are dictated at least in part by the stamping tool 50 and can vary from nanoliters to milliliters. The resulting device (e.g., device 1000 of FIG. 2d) may include any desired number of compartments 60.

In an embodiment, the tool 50 with the ridges 54 and cavities 56 is pressed against the cover film 20 of the assembly 100 (as indicated by arrow B in FIG. 2c) leaving a pattern of wells (compartments 60 of FIG. 2d), each compartment 60 holding a given (e.g., predefined) fraction of the original sample (i.e., sample 40 of the device 100 shown partially in section in FIG. 2c), as shown in FIG. 2d. In addition, each compartment 60 is surrounded by a seal 62 that fluidically isolates the portion of the sample contained in the compartment 60 from the portions of the sample contained in the other compartments 60.

In the illustrated embodiment of FIG. 2c, the tool 50 comprises a perimeter ridge 52 that defines an area that is similar in size and shape to the aperture 32 of the spacer element 50. Advantageously, the peripheral ridge seals the perimeter of the device 1000, thereby preventing leakage of sample material from the device 1000.

The external means (e.g., tool 50) may be urged onto the cover film by any manner including without limitations press tools comprising of hydraulic, pneumatic, mechanical and electrical types. In any embodiment, the external means may be urged against the cover film manually.

A relatively large number of compartments 60 are fabricated on a single device 1000 using the method of the present invention. Preferably, the device 1000 comprises 2 to 2000 compartments, more preferably about 10 to about 1000 compartments, even more preferably between about 50 to about 500 compartments, and most preferably about 100 to about 300 compartments. The device 1000 can have a population of uniformly sized compartments as shown in FIG. 2d.

In any embodiment, one or more of the plurality of compartments in a device of the present disclosure can have a volume of about 200 nL to about 10 mL. For example, one or more of the plurality of compartments can have a volume of about 200 nL, about 500 nL, about 1 µL, about 10 µL, about 50 µL, about 100 µL, about 250 µL, about 500 µL, about 1 mL, about 2 mL, about 5 mL, or about 10 mL.

In an embodiment, the device could include a plurality of lanes or other groupings, each containing compartments of a particular volume, i.e., they are not uniform throughout the device. For example, a tool as depicted in FIG. 2 of U.S. Pat. No. 6,696,286 (which is incorporated herein by reference in its entirety) can be used to form a device of the present disclosure. The corresponding device would have sets (e.g., rows) of compartments in which volumes are constant within a set, but vary between sets. The volumes can vary incrementally over an array of sets of compartments, with the smaller compartments holding sub-microliter volumes, for example, and the larger compartments holding multiple-microliter volumes. It is even possible for the largest compartments in a device to include compartments that would hold, for example, up to milliliter volumes. This feature allows for the distribution of the liquid test sample into different test volume sizes within a single device. For enumeration assays like most probable number (MPN), this feature would be beneficial and advantageous in that, for a highly concentrated sample, an appropriate volume size may be selected and MPN analysis performed using a single partitioning step in a single device without the need for serial dilutions.

The device of the present invention allows for discrete separation of a liquid test sample into a relatively large number of test microvolumes. The ability to separate a liquid sample into compartments and to perform quantitative and qualitative analysis without cross-contamination between compartments is a major advantage of the present device. Various additional fabrication methods, however, can be used to further enhance the utility of the compartments, as described below.

In any embodiment of a method according to the present disclosure, the base of a device of the present disclosure can be placed onto a compliant (i.e., flexible, yielding) surface while the external means is urged against the cover film. Advantageously, the compliant surface facilitates substantially uniform contact (and substantially uniform distribution of force) between the various contact points/surfaces of the external means and the surface of the cover film. This uniform contact ensures that the plurality of compartments is sealed in the process. Suitable compliant surfaces include, but are not limited to, a layer of flexible polymer (e.g., rubber), a layer of closed-cell or open-cell foam (e.g., polyurethane) or the like, and combinations thereof.

Figure 2E:
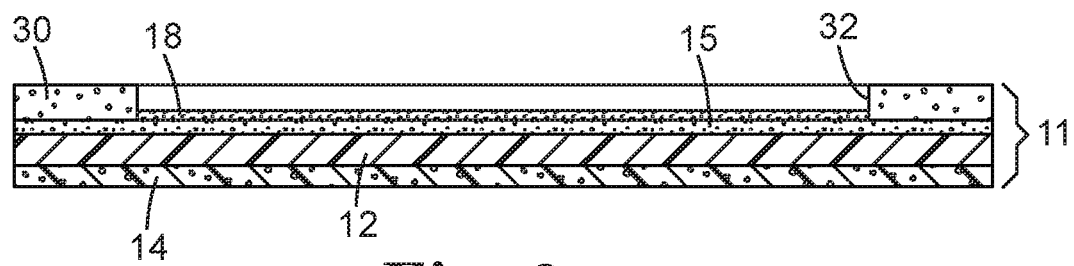
FIG. 2e is a cross sectional side view of one embodiment of the components of a device for detecting microorganisms, the device comprising a base with a compliant member.

Alternatively or additionally, in any embodiment, the base of a device of the present disclosure further comprises a compliant member. The compliant member may comprise, without limitation, the aforementioned flexible polymer layers, foam layers, and combinations thereof. FIG. 2e shows one embodiment of a base 11 that comprises a compliant member 14 coupled to the base 12. The compliant member 14 may be coupled to the substrate via any suitable means (not shown) including, for example, an adhesive, a staple, a clamp, a rivet, and a melt bond.

Figure 3A:
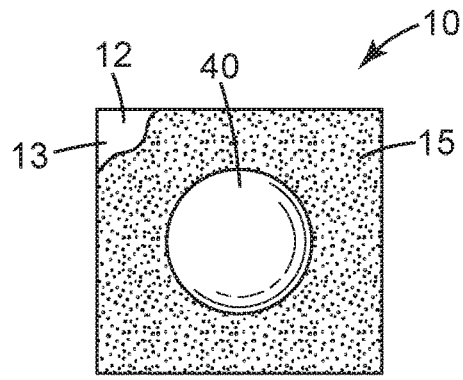
FIGS. 3a-3d are plan views showing one embodiment of the use of a substrate and a cover film to partition a liquid sample and to produce a device without a spacer element according to the present disclosure.
Figure 3B:
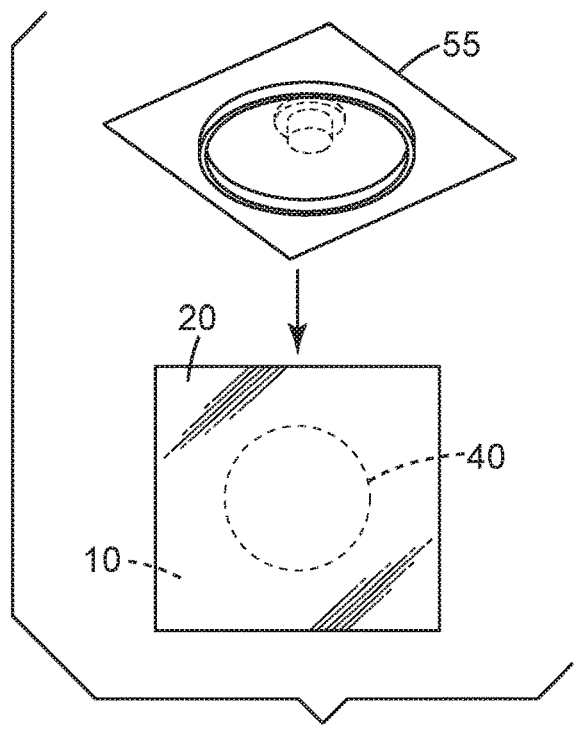
Figure 3C:
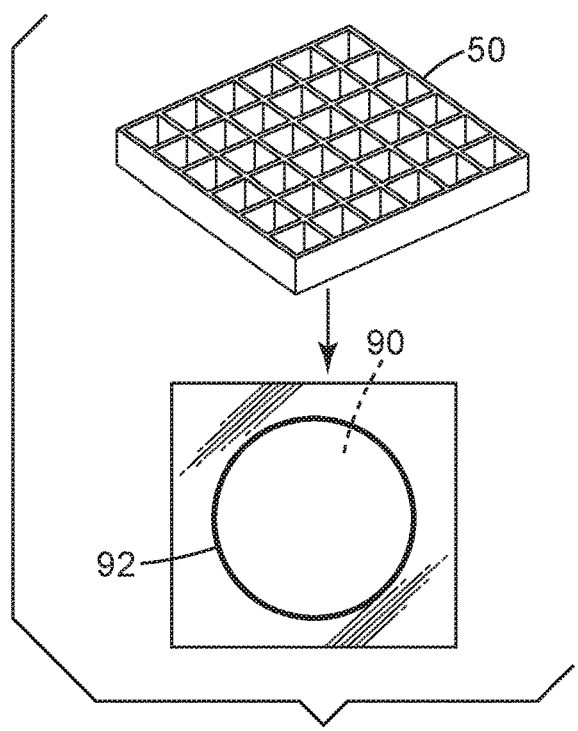
Figure 3D:
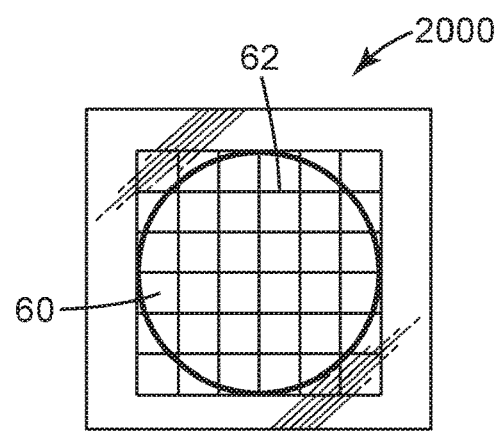

In any embodiment, a device of the present disclosure is formed via a method of partitioning a liquid sample. The device need not include a spacer element. The steps of one embodiment of a method of partitioning the aqueous sample into compartments in a device that does not have a spacer element are illustrated in FIGS. 3a-3d. A base 10 comprising a substrate 12 having a first major surface 13 is coated with a pressure-sensitive adhesive layer 15, as described herein. The base 10 can be placed on a surface (preferably, a flat, substantially level surface) with the adhesive layer 15 facing upward. A predefined volume of aqueous solution (sample 40 of FIG. 3a) to be partitioned is dispensed directly onto the adhesive layer 15, as shown in FIG. 3a.

After depositing the aqueous sample 40 onto the substrate, a cover film 20 as described herein is placed onto the sample 40 and base 10 such that the sample 40 is disposed between the cover film 20 and the adhesive layer 15 of the base 10. Optionally, the liquid sample 40 is sealed between the cover film 20 and the adhesive layer 15 of the base 10 by forming a perimeter seal surrounding the liquid sample 40 disposed between the cover film 20 and the adhesive layer 15 of the base 10. The perimeter seal (e.g., perimeter seal 92 shown in FIG. 3c) is formed by urging a predefined portion of the of the cover film 20 against the adhesive layer 15. This can be done using any suitable perimeter-forming external means such as, for example, a tool 55 having a ridge 56 surrounding a cavity 57. The cavity 57 should define a volume that is at least as large as, a preferably about equal to, the volume of the aqueous sample 40. Thus, when the tool 55 is urged against the cover film, it distributes the sample 40 over a predefined area of the base 10. The ridge 56 of the tool 55, when urged against the cover film 20, causes contact between the cover film 20 and the adhesive layer 15, thereby forming a perimeter seal 90 that defines a sample-holding are (i.e., a chamber 90). In any embodiment, the chamber 90 has a predetermined volume defined by the cavity 57 of the tool 55. When the volume of the cavity 57 is approximately equal to the volume of the liquid sample 40, air is substantially excluded during formation of the perimeter seal 92. One embodiment of a suitable tool 55 form forming the perimeter seal 92 is a plastic spreading device such as the PETRIFILM Yeast and Mold spreader available from 3M Company (St. Paul, MN).

In an alternative embodiment (not shown), the perimeter seal 92 can be formed manually by urging a blunt object (e.g., a pencil tip, an eraser tip) against the cover film to trace a perimeter seal around the liquid sample. It is contemplated that the perimeter seal 92 can take the form of any one of a variety of shapes including, without limitation, a circle, an oval, a polygon, a square, a rectangle, a hexagon, an octagon, and an obround.

After the optional perimeter seal 92 is formed, a partition-forming external means (e.g., tool 50 of FIG. 3c) is urged against the cover film 20 to bring predefined portions of the cover film 20 into contact with the adhesive layer 15 to form a plurality of compartments 60. Seals 62 are formed where the predefined portions of the cover film 20 contact the adhesive layer 15. The seals substantially prevent liquid communication between the compartments. A non-limiting example of a suitable external means for forming compartments 62 is a plastic 384-well microtiter plate (Untreated black #242764, Nalge Nunc International; Rochester, NY). The external means can be urged against the cover film 20, for example, by using manual pressure or by using an air press (e.g., a Model A-0019 air press available from Janesville Tool and Manufacturing, Inc.; Milton, WI). The amount of force used to form the seals should be enough force to ensure sufficient contact between the cover film and the adhesive layer to form the seals.

Using an external means that has approximately the same shape and dimensions as the chamber 90 preferably can ensure that each compartment of the plurality of compartments created by the method has a predefined (optionally, substantially uniform) volume. However, as illustrated in FIGS. 3a-3d, this is not mandatory.

Figure 4A:
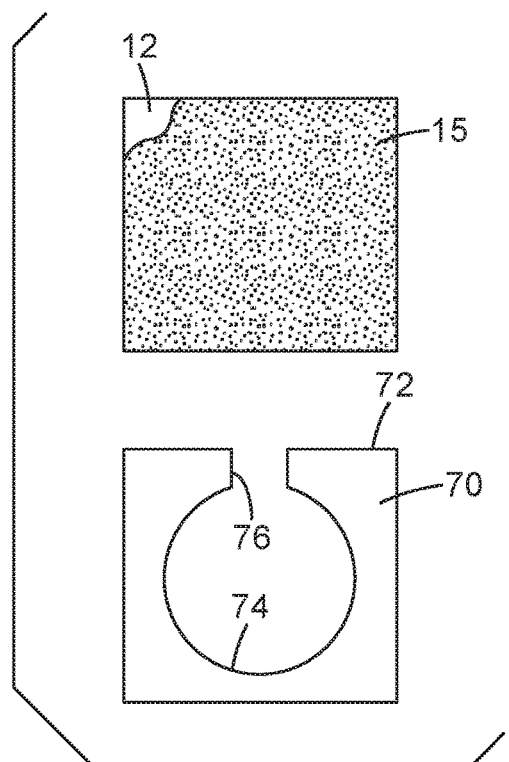
FIGS. 4a-4e are plan views showing one embodiment of the construction of a pouch for analyzing a sample according to the present disclosure.

In another aspect, the present disclosure provides a pouch for partitioning a liquid sample (e.g., an aqueous liquid sample. FIG. 4a shows a plan view, partially in section, of some of the components used to make a pouch according to the present disclosure. In any embodiment, a substantially planar substrate 12 has a layer or pressure-sensitive adhesive 15 coated on a major surface. Suitable substrates 12 and adhesives 15 are described hereinabove. Prior to applying a coating over the adhesive 15, a sheet-like mask 70 is applied (e.g., laminated) to the adhesive 15 on the substrate 12. The mask 70 has a peripheral edge 72, a central opening 74, and a gap 76 extending from the opening 74 to the peripheral edge 72. When placed on the substrate 12, the opening 74 and gap 76 expose a portion of the adhesive 15. Although shown as having a circular shape, it is contemplated that the opening 74 may have any of a number of suitable shapes (e.g., circular, square, oval, oblong, rectangular, polygonal, or the like).

Figure 4B:
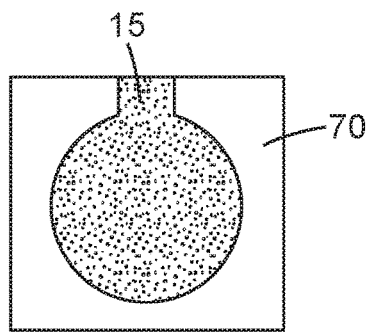
Figure 4C:
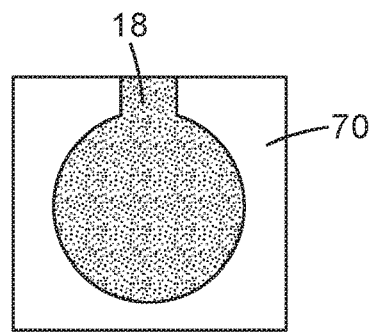

The mask 70 can be fabricated from a variety of materials including, for example, sheets of paper or plastic film. Preferably, the mask 70 is coated with a low-adhesion backsize on the side that is placed against the adhesive 15. The low-adhesion backsize (not shown) facilitates removal of the mask from the adhesive 15 without disrupting the bond between the adhesive 15 and the substrate 12. After the mask 70 is applied to the adhesive 15, a secondary coating 18 (e.g., a coating of a powder material such as a reagent or particles as described hereinabove) is applied to the exposed adhesive 18. FIG. 4c shows the secondary coating 18 adheres to the portions of the adhesive that are not covered by the mask 70. In any embodiment, the secondary coating 18 comprises a water-soluble reagent as described herein. In any embodiment, the secondary coating comprises a plurality of particles (e.g., glass bubbles such as K37 glass bubbles available from 3M Company; St. Paul, MN) having a mean particle diameter less than or equal to the thickness of the layer of the adhesive 18.

Figure 4D:
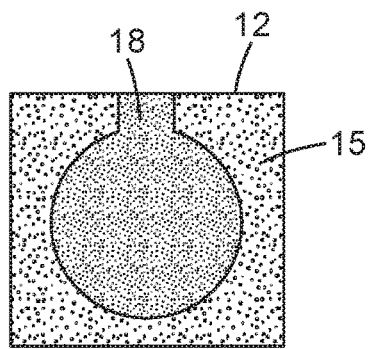
Figure 4E:
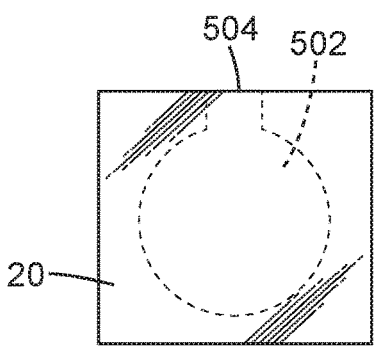

After applying the secondary coating 18, excess powder optionally can be removed (e.g., by vibration) and the mask 70 is removed. Removing the mask 70 exposes the remaining adhesive 15 on the substrate 12, as shown in FIG. 4d. To complete the preparation of a pouch 500 according to the present disclosure, a cover film 20 dimensioned to cover the exposed adhesive 15 is laminated (e.g., using a roller, not shown) to the adhesive, as shown in FIG. 4e. The pouch 500 comprises an interior reservoir 502 into which a liquid sample (not shown) is introduced through a port 504 (i.e., opening) along an edge of the pouch 500.

A pouch 500 according to the present disclosure can be used in a method of partitioning a sample. FIGS. 5a-5d show one embodiment of the steps that are used to partition a liquid sample using the pouch 500 of FIG. 4e.

Figure 5A:
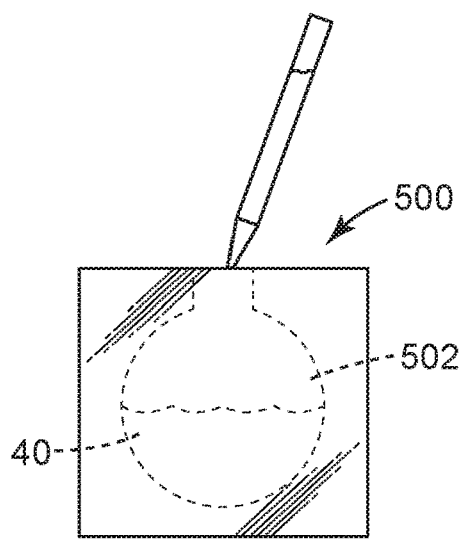
FIGS. 5a-5d are plan views of one embodiment of a method of using the pouch of FIG. 4e to partition a liquid sample.
Figure 5B:
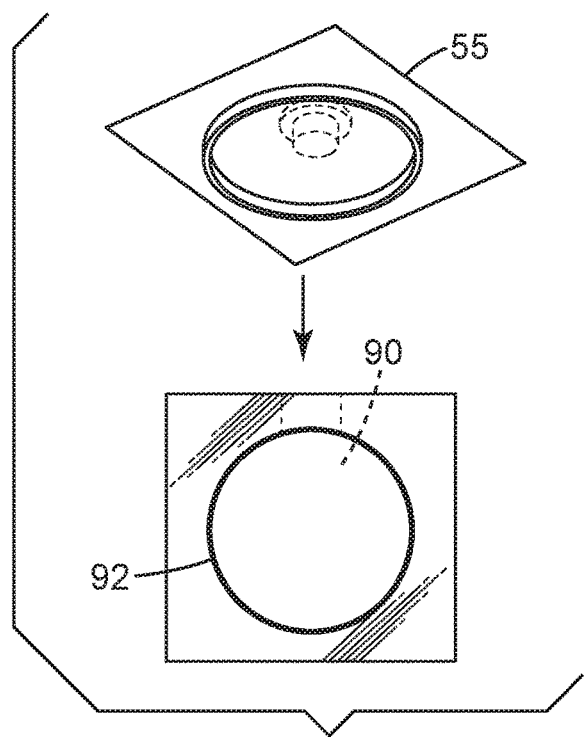
Figure 5C:
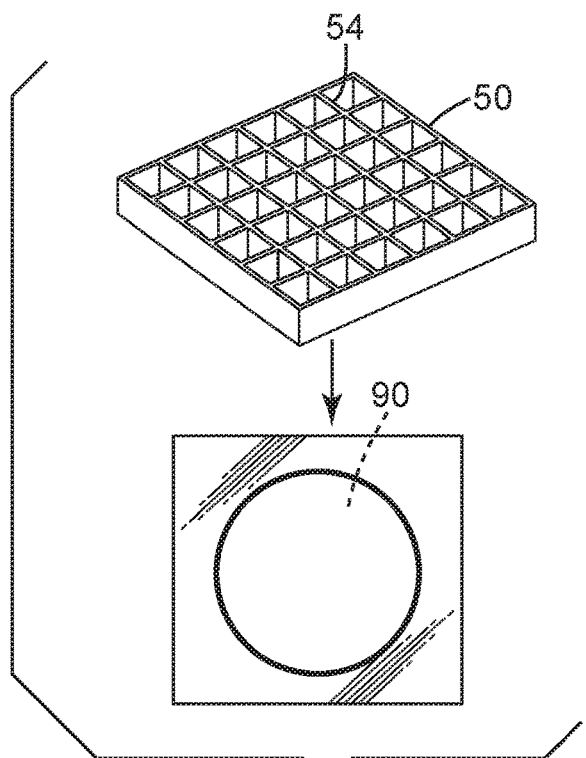
Figure 5D:
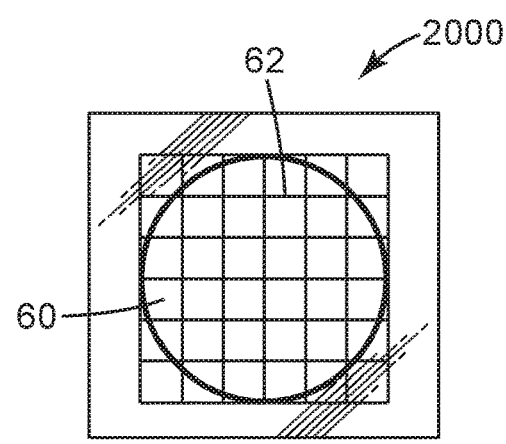

A liquid sample 40 (e.g., an aqueous sample suspected of containing a biological material (e.g., a microorganism or biomolecule) is introduced (e.g., via pipet) into the reservoir 502 of the pouch 500, as shown in FIG. 5a. If the secondary coating (not shown) in the reservoir 502 comprises a water-soluble reagent, introduction of the liquid sample 40 dissolves the reagent and exposes the adhesive (not shown so that it can bond with the cover film of the pouch 502. Optionally, a spreading device 55 (e.g., a PETRIFILM yeast and mold plate spreader available from 3M Company; St. Paul, Minnesota) can be urged against the cover film of the pouch 500 to spread the liquid throughout the reservoir 502, to push air out of the reservoir 502 (via the port), and to form a peripheral seal 92 around a single, liquid-filled chamber 90, as shown in FIG. 5b. An external means (e.g., tool 50) is urged against the liquid-filled reservoir (not shown) or liquid-filled compartment 90 (as shown in FIG. 5c), as described above, to form the device 2000 shown in FIG. 5d. The device 2000 comprises a plurality of liquid-filled compartments 40, each compartment isolated from adjacent compartments via one or more seal 42 according to the pattern of ridges 54 defined by the tool 50 as described herein.

Accordingly, the present invention provides a method for detecting a microorganism in a test sample. Non-limiting examples of suitable test samples include solids, semi-solids, gelatinous materials, particulate suspensions, solutions, liquids, and combinations thereof. Solid or semi-solid samples can be homogenized and/or suspended in an aqueous medium (e.g., sterile water, a buffer, a nutrient medium) before they are introduced into a device or pouch of the present disclosure. The liquid or liquefied test sample may be deposited directly on to the substrate coated with adhesive and, optionally a secondary coating. The sample is spread out and the device is formed as described herein, resulting in the partitioning of the liquid into a plurality of closed compartments disposed between the substrate and the cover film by efficient sealing of the top and substrates with the aid of the PSA. The qualitative and quantitative analysis of the partitioned samples can be conducted on at least one compartment using the methods known to a person skilled in the art.

Quantitative analysis include without limitation enumeration, quantification, counting and measurement of the microorganisms or biomolecules in the sample. Biomolecules may include without limitation polysaccharides, lipids, nucleic acids, DNA, RNA, metabolites, vitamins, hormones and amino acids. Qualitative analysis include without limitation detection, culturing, isolation, identification and purification of microorganisms or biomolecules.

In another embodiment, the invention relates to a method for culturing a microorganism in a liquid test sample. The method is similar to the method described above except that the partitioned samples include a nutrient growth medium and are allowed to incubate under conditions for a time sufficient to facilitate at least one cell division of the microorganism. For the culturing of anaerobic microorganisms, the device with the partitioned samples may be kept in an anaerobic chamber to maintain an anaerobic environment in the compartments.

After distribution of the sample into compartments, various assays may be carried out depending on desired uses. For microbial detection or enumeration, the assay device may be incubated for a time sufficient to permit at least one cell division cycle of the microorganism. For these purposes, the device is generally incubated at about 25° C. to about 45° C., more preferably at about 30° C. to about 37° C. The incubation time for microorganism detection will vary. The detection time will also vary depending on the growth rate, the detection system (e.g., indicator reagents) used, and the number of microorganisms present in the sample.

The liquid test sample may be any sample of interest, from any source. The liquid test sample may include selective nutrient growth media for the microorganism of interest, and/or an indicator substance that produces a signal in the presence of the growing microorganism. Preferably, nutrient growth media is present as a coating on the substrate, in amounts sufficient to achieve desired concentrations when a volume of the liquid test sample is distributed onto the substrate. Such a coating may be achieved, for example, by placing or distributing a solution of the nutrient media onto the substrate and drying the solution to produce a coating or deposition of the nutrient medium on the film. Components of the media may be present in the adhesive coated on the substrate. The media ultimately diffuses into the sample when it comes into contact with the liquid sample.

A wide variety of selective growth media for a wide variety of microorganisms of interest is known, as is a wide variety of indicator substances for a wide variety of microorganisms, and any of these media or indicator substances are suitable for use in the method of the invention. An advantage of the present invention is that soluble indicators can be used, since diffusion is prevented by confinement of the aqueous biological sample in the sealed compartments.

In other embodiments, the compartments may contain a coating of nutrient medium, and the nutrient medium may further include at least one indicator substance. Alternatively, the liquid test sample may include at least one indicator substance. In either case, the indicator substance may be any indicator substance capable of providing a detectable signal in the liquid test sample. Such indicators include, but are not limited to, chromogenic indicators, fluorescent indicators, luminescent indicators, and electrochemical indicators. For purposes of this application, the term "electrochemical" means a chemical indicator that changes the resistance or conductance of the sample upon reaction with a microorganism.

The assay reagents can be immobilized in the substrate by any of numerous methods for immobilizing assay reagents on solid substrates known to those of skill in the art. Such methods include for example drying down assay reagent-containing liquids, and other methods for non-covalently attaching biomolecules and other assay reagents to a solid substrate. Alternatively, various methods may be employed to covalently attach assay reagents to the substrate by methods well known to those of skill in the art.

Fluorogenic indicators which are detected at relatively low concentrations may be suitably employed. Suitable indicators include 4-methylumbelliferyl phosphate, and 4-methylumbelleferyl —B-D-glucopyranoside, L-phenyl-alanine-7-amido-4-methylcoumarin. Others may include 4-methylumbelliferyl acetate and 4-methylumbelliferyl sulfate.

In another aspect, a kit for the device is fabricated. In any embodiment, the kit comprises the following components: (i) a substrate having a first major surface with a layer of a water-insoluble pressure sensitive adhesive coated thereon and (ii) a composite polymeric film. The substrate can be any suitable substrate for the device as described herein. The composite polymeric film comprises ethylene vinyl acetate copolymer, a linear copolymer of ethylene and a higher alkene, and a tackifier. The tackifier is selected from a group consisting of a low molecular weight polyisobutene, poly-terpenes, amorphous polypropylene, and microcrystalline wax. In any embodiment, the composite polymeric film has an elastic recovery less than or equal to 20%.

In any embodiment, the kit comprises the following components: (i) a substrate having a first major surface with a layer of a water-insoluble pressure sensitive adhesive adhered thereto, the substrate and adhesive as described herein, and (ii) a polymeric film having an elastic recovery of less than or equal to 20%, as described herein.

In any embodiment of the kit, the substrate and/or the polymeric film is substantially planar. In any embodiment of the kit, the substrate and/or the polymeric film is substantially flat. In any embodiment of the kit, the pressure sensitive adhesive comprises silicone polyurea. In any embodiment of the kit, the substrate further comprises a secondary coating disposed on at least a portion of the adhesive. In any embodiment of the kit, the secondary coating comprises a powdered nutrient and/or a plurality of glass bubbles. In any embodiment of the kit, the secondary coating is substantially water-free. In any embodiment of the kit, a spacer element is coupled to the first major surface of the substrate, as described hereinabove. In any embodiment of the kit, the composite polymeric film is attached to the substrate, wherein the spacer element, if present, is disposed between the substrate and the cover film.

Additional components of any kit according to the present disclosure may comprise sample spreading tools, sample area defining objects and stamping tools of various sizes and shapes. The kit may additionally comprise instruction manual for ease of use.

There are a variety of alternative techniques and procedures available to those of skill in the art that would similarly permit one to successfully practice the intended invention. All specific materials and methods described below, in whole or in part, fall within the scope of the invention. These specific compositions, materials, and methods are not intended to limit the invention, but merely to illustrate specific embodiments falling within the scope of the invention. One skilled in the art may develop equivalent materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

EXEMPLARY EMBODIMENTS

Embodiment A is a device, comprising:
a base comprising a substrate, the substrate having a first major surface;
a pressure sensitive adhesive adhered to at least a portion of the first major surface;
a polymeric cover film coupled to the substrate via the adhesive;
wherein the cover film is a composite film comprising a polymer and a tackifier;
wherein the composite film comprises ethylene vinyl acetate copolymer, a linear copolymer of ethylene and a higher alkene, and the tackifier;
a plurality of closed compartments disposed between the substrate and the cover film, each compartment of the plurality defined by a seal that prevents liquid communication with at least one other compartment of the plurality; and
an aqueous liquid disposed in two or more of the closed compartments;
wherein the seal is formed by contact between the cover film and the pressure-sensitive adhesive.

Embodiment B is the device of Embodiment A, wherein the tackifier is selected from a group consisting of a low molecular weight polyisobutene, polyterpenes, amorphous polypropylene, and microcrystalline wax.

Embodiment C is the device of Embodiment A or Embodiment B, wherein the cover film has an elastic recovery less than or equal to 20%.

Embodiment D is a device, comprising:
a base comprising a substrate, the substrate having a first major surface;
a pressure sensitive adhesive adhered to at least a portion of the first major surface;
a polymeric cover film coupled to the substrate via the adhesive, the cover film having an elastic recovery less than or equal to 20%;
a plurality of closed compartments disposed between the substrate and the cover film, each compartment of the plurality defined by a seal that prevents liquid communication with at least one other compartment of the plurality; and
an aqueous liquid disposed in two or more of the closed compartments; wherein the seal is formed by contact between the cover film and the pressure-sensitive adhesive.

Embodiment E is the device of any one of the preceding Embodiments, wherein the substrate is water insoluble.

Embodiment F is the device of any one of the preceding Embodiments, wherein the seal prevents liquid communication between any two compartments of the plurality.

Embodiment G is the device of any one of the preceding Embodiments, wherein the first major surface is substantially planar.

Embodiment H is the device of any one of the preceding Embodiments, wherein the substrate has a thickness of at least about 0.02 mm.

Embodiment I is the device of Embodiment H, wherein the substrate has a thickness less than or equal to 5 mm.

Embodiment J is the device of Embodiment H, wherein the substrate has a thickness less than or equal to 2 mm.

Embodiment K is the device of any one of the preceding Embodiments, wherein the substrate is made of a material selected from the group consisting of polypropylene, polyurethane, polyethylene, polyester, polyimide, fluoropolymers, polycarbonate, polystyrene, a derivative of any one of the foregoing materials, and a combination of any two or more of the foregoing materials.

Embodiment L is the device of Embodiment K, wherein the material is polypropylene, wherein the polypropylene is biaxially-oriented polypropylene.

Embodiment M is the device of any one of the preceding Embodiments, wherein the substrate is comprises a metal foil.

Embodiment N is the device of Embodiment M, wherein the metal foil comprises aluminum, copper, or steel.

Embodiment O is the device of Embodiment M or Embodiment N, wherein the metal foil comprises a metal foil-polymer laminate.

Embodiment P is the device of any one of the preceding Embodiments, wherein the pressure sensitive adhesive retains its adhesive property when in contact with an aqueous liquid.

Embodiment Q is the device of any one of the preceding Embodiments, wherein the pressure sensitive adhesive comprises an elastomer and a tackifier.

Embodiment R is the device of any one of Embodiments A through P, wherein the pressure sensitive adhesive is silicone polyurea adhesive.

Embodiment S is the device of any one of the preceding Embodiments, wherein the thickness of the pressure sensitive adhesive is at least about 0.02 mm.

Embodiment T is the device of Embodiment S, wherein the thickness of the pressure sensitive adhesive is less than or equal to 0.2 mm.

Embodiment U is the device of any one of the preceding Embodiments, wherein the cover film is a composite film comprising a polymer and a tackifier.

Embodiment V is the device of any one of the preceding Embodiments, wherein the cover film is a self-sealing, moldable and flexible film.

Embodiment W is the device of any one of the preceding Embodiments, wherein the thickness of at least a portion of the cover film is 0.01 mm to 0.5 mm.

Embodiment X is the device of Embodiment W, wherein the thickness of at least a portion of the cover film is 0.10 mm to 0.25 mm.

Embodiment Y is the device of any one of the preceding Embodiments, wherein the thickness of at least a portion of the cover film when stretched is 0.01 mm to 0.20 mm.

Embodiment Z is the device of any one of the preceding Embodiments, wherein the aqueous liquid comprises a biological sample.

Embodiment AA is the device of Embodiment Z, wherein the biological sample is for microbiological analysis or biochemical analysis.

Embodiment AB is the device of Embodiment Z, wherein the biological sample is a food sample, clinical sample, an environmental sample, or a waste water sample.

Embodiment AC is the device of any one of the preceding Embodiments, wherein the aqueous liquid in each compartment has a volume of 200 nL to 10 mL.

Embodiment AD is the device of any one of the preceding Embodiments, wherein the aqueous liquid in all of the compartments has a total volume in the range of 50 μL to 100 mL.

Embodiment AE is the device of any one of the preceding Embodiments, wherein the device further comprises a spacer element disposed between the substrate and the cover film.

Embodiment AF is the device of Embodiment AE, wherein the spacer element is attached to the substrate.

Embodiment AG is the device of any one of the preceding Embodiments, wherein the device further comprises a secondary coating disposed on at least a portion of the pressure sensitive adhesive.

Embodiment AH is the device of Embodiment AG, wherein the secondary coating consists essentially of dry powder.

Embodiment AI is the device of Embodiment AG or Embodiment AH, wherein the secondary coating is selected from the group consisting of nutrients, chemicals, dyes, proteins, enzymes and antibodies.

Embodiment AJ a method for partitioning liquid comprising:
depositing a predefined volume of liquid between a substrate and a polymeric cover film wherein said substrate is coated with water-insoluble pressure sensitive adhesive;
  wherein the cover film is a composite film comprising a polymer and a tackifier;
  wherein the composite film comprises ethylene vinyl acetate copolymer, a linear copolymer of ethylene and a higher alkene, and the tackifier; and
urging an external means against the cover film to bring discrete regions of the cover film in contact with the pressure sensitive adhesive of the substrate resulting in the partitioning of the liquid into a plurality of closed compartments disposed between the substrate and the cover film.

Embodiment AK is the method of Embodiment AJ, wherein the tackifier is selected from a group consisting of a low molecular weight polyisobutene, polyterpenes, amorphous polypropylene, and microcrystalline wax.

Embodiment AL is the method of Embodiment AJ or Embodiment AK, wherein the cover film has an elastic recovery less than or equal to 20%.

Embodiment AM is a method for partitioning liquid comprising:
depositing a predefined volume of liquid onto a first surface of a substrate such that the liquid sample is disposed between the first surface and a polymeric cover film, wherein said first surface is coated with water-insoluble pressure sensitive adhesive and said cover film has an elastic recovery less than or equal to 20%; and
urging an external means against the cover film to bring discrete regions of the cover film in contact with the pressure sensitive adhesive of the substrate resulting in the partitioning of the liquid into a plurality of closed compartments disposed between the substrate and the cover film.

Embodiment AN is the method of any one of Embodiments AJ through AM wherein, prior to urging the external means against the cover film, the substrate and/or the cover film are substantially flat.

Embodiment AO is the method of any one of Embodiments AJ through AN, wherein the external means comprises a patterned surface having a plurality of cavities.

Embodiment AP is the method of any one of Embodiments AJ through AO, wherein the substrate further comprises a secondary coating disposed on the adhesive.

Embodiment AQ is the method of Embodiment AP, wherein the secondary coating is selected from the group consisting of nutrients, chemicals, dyes, proteins, enzymes and antibodies.

Embodiment AR is a method for analyzing a liquid sample, comprising:
depositing a predefined volume of liquid onto a first surface of a substrate such that the liquid sample is disposed between the first surface and a polymeric cover film wherein said first surface is coated with water-insoluble pressure sensitive adhesive;
  wherein the cover film is a composite film comprising a polymer and a tackifier;
  wherein the composite film comprises ethylene vinyl acetate copolymer, a linear copolymer of ethylene and a higher alkene, and the tackifier;
urging an external means against the cover film to bring discrete regions of the cover film in contact with the pressure sensitive adhesive of the substrate resulting in the partitioning of the liquid into a plurality of closed compartments disposed between the substrate and the cover film; and
conducting a quantitative analysis or a qualitative analysis of at least one closed compartment of the plurality.

Embodiment AS is the method of Embodiment AR, wherein the tackifier is selected from a group consisting of a low molecular weight polyisobutene, polyterpenes, amorphous polypropylene, and microcrystalline wax.

Embodiment AT is the method of Embodiment AR or Embodiment AS, wherein the cover film has an elastic recovery less than or equal to 20%.

Embodiment AU is a method for analyzing a liquid sample comprising:
depositing a liquid sample onto a first surface of a substrate such that the liquid sample is disposed between the first surface and a polymeric cover film wherein said first surface is coated with water-insoluble pressure sensitive adhesive and said polymeric cover film has an elastic recovery less than or equal to 20%;
(ii) urging an external means against the cover film to bring discrete regions of the cover film in contact with the pressure sensitive adhesive of the substrate resulting in the partitioning of the liquid into a plurality of closed compartments disposed between the substrate and the cover film; and
conducting a quantitative analysis or a qualitative analysis of at least one closed compartment of the plurality.

Embodiment AV is the method of any one of Embodiments AR through AU wherein, prior to urging the external means against the cover film, the substrate and/or the cover film are substantially flat.

Embodiment AW is the method of any one of Embodiments AR through AV, wherein the quantitative analysis comprises enumeration of microorganisms or biomolecules in the sample.

Embodiment AX is the method of Embodiment AW, wherein the biomolecules are selected from a group consisting of proteins, polysaccharides, lipids, nucleic acids, DNA, RNA, metabolites, vitamins, hormones and amino acids.

Embodiment AY is the method of any one of Embodiments AR through AX, wherein the qualitative analysis comprises detection, culturing, isolation, identification or purification of a microorganism or a biomolecule in the sample.

Embodiment AZ is a method for culturing a microorganism, comprising:
depositing a predefined volume of liquid onto a first surface of a substrate such that the liquid sample is disposed between the first surface and a polymeric cover film wherein said first surface is coated with water-insoluble pressure sensitive adhesive;
wherein the cover film is a composite film comprising a polymer and a tackifier;
wherein the composite film comprises ethylene vinyl acetate copolymer, a linear copolymer of ethylene and a higher alkene, and the tackifier;
urging an external means against the cover film to bring discrete regions of the cover film in contact with the pressure sensitive adhesive of the substrate resulting in the partitioning of the liquid into a plurality of closed compartments disposed between the substrate and the cover film; and
incubating the liquefied and partitioned sample, under conditions to facilitate at least one cell division of said microorganism.

Embodiment BA is the method of Embodiment AZ, wherein the tackifier is selected from a group consisting of a low molecular weight polyisobutene, polyterpenes, amorphous polypropylene, and microcrystalline wax.

Embodiment BB is the method of Embodiment AZ or Embodiment BA, wherein the cover film has an elastic recovery less than or equal to 20%.

Embodiment BC is a method for culturing a microorganism comprising:
mixing a sample with a liquid nutrient medium to render it liquefied;
depositing the liquefied sample onto a first surface of a substrate such that the liquid sample is disposed between the first surface and a polymeric cover film wherein said first surface is coated with water-insoluble pressure sensitive adhesive and said polymeric cover film has an elastic recovery less than or equal to 20%;
urging an external means against the cover film to bring discrete regions of the cover film in contact with the pressure sensitive adhesive of the substrate resulting in the partitioning of the liquid into a plurality of closed compartments disposed between the substrate and the cover film; and
incubating the liquefied and partitioned sample under conditions to facilitate at least one cell division of said microorganism.

Embodiment BD is the method of any one of Embodiments AZ through BC wherein, prior to urging the external means against the cover film, the substrate and/or the cover film are substantially flat.

Embodiment BE is the method of any one of Embodiments AZ through BD, wherein the microorganism is aerobic or anaerobic.

Embodiment BF is a kit, comprising:

a substrate having a first major surface with a layer of a water-insoluble pressure sensitive adhesive coated thereon; and
a composite polymeric film;
wherein the polymeric film comprises ethylene vinyl acetate copolymer, a linear copolymer of ethylene and a higher alkene, and a tackifier;
wherein the tackifier is selected from a group consisting of a low molecular weight polyisobutene, polyterpenes, amorphous polypropylene, and microcrystalline wax.

Embodiment BG is the kit of Embodiment BF, wherein the composite polymeric film has an elastic recovery of less than or equal to 20%.

Embodiment BH is a kit comprising:
a substrate having a first major surface with a layer of a water-insoluble pressure sensitive adhesive adhered thereto; and
a polymeric film having an elastic recovery of less than or equal to 20%.

Embodiment BI is the kit of any one of Embodiments BF through BH, wherein the substrate and/or the polymeric film is substantially planar.

Embodiment BJ is the kit of any one of Embodiments BF through BI, wherein the pressure sensitive adhesive comprises silicone polyurea.

Embodiment BK is the kit of any one of Embodiments BF through BJ, wherein the substrate further comprises a secondary coating disposed on at least a portion of the adhesive.

Embodiment BL is the kit of Embodiment BK, wherein the secondary coating comprises a powdered nutrient and/or a plurality of glass bubbles.

Embodiment BM is the kit of any one of Embodiments BF through BL, wherein a spacer element is coupled to the first major surface of the substrate.

Embodiment BN is the kit of any one of Embodiments BF through BM:
wherein the polymeric film is attached to the substrate;
wherein the spacer element, if present, is disposed between the substrate and the cover film.

Embodiment BO is a pouch, comprising:
a substrate;
a composite polymeric film attached to the substrate;
a reservoir disposed between the first layer and the second layer; and
a port through which a liquid can be introduced into the reservoir;
wherein, in the reservoir, the substrate includes a pressure-sensitive adhesive layer adhered to the substrate and a substantially water-free secondary layer coated onto the adhesive layer;
wherein the secondary layer prevents adhesion between the adhesive and the composite polymeric film;
wherein the polymeric film comprises ethylene vinyl acetate copolymer, a linear copolymer of ethylene and a higher alkene, and a tackifier;
wherein the tackifier is selected from a group consisting of a low molecular weight polyisobutene, polyterpenes, amorphous polypropylene, and microcrystalline wax.

Embodiment BP is the pouch of Embodiment BO, wherein the composite polymeric film has an elastic recovery of less than or equal to 20%.

Embodiment BQ is a pouch, comprising:
a substrate;
a polymeric film attached to the substrate;
a reservoir disposed between the substrate and the polymeric film; and a port through which a liquid can be introduced into the reservoir;

wherein, in the reservoir, the substrate includes a pressure-sensitive adhesive layer adhered to the substrate and a substantially water-free secondary layer coated onto the adhesive layer;

wherein the secondary layer prevents adhesion between the adhesive and the composite polymeric film;

wherein the polymeric film has an elastic recovery of less than or equal to 20%.

Embodiment BR is the pouch of any one of Embodiments BO through BQ, wherein the secondary coating comprises a powder.

Embodiment BS is the pouch of any one of Embodiments BO through BR, wherein the secondary coating comprises a nutrient, a reagent for indicating microbial growth, or a selective agent.

Embodiment BT is the pouch of any one of Embodiments BN through BS, wherein the secondary coating comprises a plurality of water-insoluble particles.

Embodiment BU is the pouch of Embodiment BT, wherein the water-insoluble particles comprise glass bubbles.

Embodiment BV is the pouch of Embodiment BT or Embodiment BU, wherein the water-insoluble particles have a mean diameter, wherein the adhesive layer has a thickness, wherein the mean diameter is less than or equal to the thickness.

Embodiment BW is a kit comprising the pouch of any one of Embodiments BQ through BX.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Example 1: Preparation of Sealed Device and Partitioning of Aqueous Sample in the Sealed Device Preparation of the Substrate and Cover Film Biaxially oriented polypropylene of 0.05 mm (2 mil) thickness, having a substantially planar first surface, was used (BOPP, 2 mil) as the substrate. On the first surface, the film was coated with a water-insoluble, silicone based pressure sensitive adhesive, silicone polyurea, of 0.05 mm (2 mil) thickness. The water-insoluble silicone polyurea adhesive was prepared according to the method described in U.S. Pat. Nos. 5,461,134 and 6,007,914; which are both incorporated herein by reference in their entirety.

For the hydrophobic cover film, plastic paraffin film (PARAFILM M 4 mil (0.1 mm) film, Bemis Flexible Packaging Company; Oshkosh, WI) of 0.1 mm thickness was used.

Partitioning of the Aqueous Sample into Compartments

Aqueous solutions were prepared by diluting an overnight culture of Escherichia coli (ATCC #25922, American Type Tissue Collection; Manassas, Virginia) in BACTO™ Trypticase Soy Broth (Becton, Dickinson and Company; Franklin Lakes, New Jersey) with 0.5 mg/ml 4-methylumbelliferyl-β-D-glucuronide (Sigma-Aldrich Corp.; St. Louis, MO). The test solutions had about 1-100 bacteria per microliter.

The steps in the process of partitioning the aqueous sample into compartments are illustrated in FIGS. 3a-3d. The adhesive-coated substrate (i.e., the base 10 of FIG. 3a) was placed on a flat surface with the adhesive 15 facing upward and 1 ml of test aqueous solution (sample 40 of FIG. 3a) was dispensed directly onto the adhesive-coated base, as shown in FIG. 3a.

After adding the aqueous sample onto the substrate, the cover film 20 was then carefully placed onto the sample 40 and base 10 and a plastic spreading device (a PETRIFILM yeast and mold plate spreader, 3M Company; St. Paul, Minnesota) was urged against the cover film 20 (as indicated by arrow B in FIG. 3b) to spread the liquid out and seal the liquid into a circular chamber (chamber 90 of FIG. 3c), having a 6 cm diameter, between the cover film 20 and the base. The chamber 90 was bordered by a perimeter seal 92 that joined the cover film 20 to the base 10.

A plastic 384-well microtiter plate (Untreated black #242764, Nalge Nunc International; Rochester, NY) (tool 50 of FIG. 3c) was placed on top of the culture device with the openings of the wells facing down and an air press (Model A-0019, Janesville Tool and Manufacturing, Inc.; Milton, WI) was used to press the microtiter plate down using moderate force (i.e., using just enough force to ensure contact between the cover film and the adhesive layer), deforming the cover film up into the cavities of the microtiter plate and sealing the cover film to the substrate in the area between the wells, thereby forming the inoculated partitioned device 2000 of FIG. 3d.

The compartments 60 (FIG. 3d) were formed by the creation of seals 62 at the area of contact between the cover film and the pressure-sensitive adhesive of the base. The resulting seals 62 formed leak proof compartments.

After stamping, each device contained approximately 140 individually sealed wells that each contained between 5 and 10 microliters of sample. Deformation of the cover film appeared to be very uniform with >95% of the wells being completely liquid-filled with no visible air bubbles. The stamped culture device was subsequently removed from the 384-well plate.

Example 2: Compartments Having Acrylate Adhesive-Coated Aluminum Foil as Bottom Layer A culture device was constructed as described in Example 1 above, with exceptions as noted in the following paragraph.

For the substrate, 9792R foil tape (3M Company, St. Paul, MN) was used. This foil (0.036 mm thick) is a dead soft aluminum foil coated on one side with a 3M select diagnostic acrylate adhesive. The adhesive is approximately 0.027 mm thick. The foil is opaque, pierceable and the adhesive is very compatible to bioassays.

The cover film was fabricated using PARAFILM M plastic paraffin film, as described in Example 1. The construction of this device permitted a 1 μl capillary pipette to be inserted through the foil tape in order to extract sample from a any of the individual compartments (not shown). Advantageously, this can permit subsequent tests (e.g., biochemical, immunological, enzymatic tests) to be performed using at least a portion of the contents of a particular compartment.

Example 3: Detection of Bacterial Growth—Qualitative Analysis

Incubation and Detection of Growth of Microorganism in Compartments

The stamped culture device of Example 1 having the partitioned samples in the sealed compartments was incubated at 37° C. for 24 hours.

Aerobic count (AC) PETRIFILM plates (3M Company; St. Paul, MN) were used as a comparator with 1 ml of the same test solution having been inoculated onto the film according to the manufacturer's instructions, spread, and incubated at 37° C. for 24 hours.

After the incubation, the liquid-filled compartments were observed for growth of bacteria as evidenced by fluorescence in one or more compartment when the device was place under UV illumination. Enzymatic cleavage of the non-fluorescent 4-methylumbelliferyl-β-D-glucuronide (MUG) to a fluorescent product by $E.\ coli$ β-glucuronidase indicated positive growth in a compartment. The hydrolysis of the 4-methylumbelliferyl-β-D-glucuronide (MUG) fluorogenic substrate was detected using stereomicroscope. A stereomicroscope (Zeiss Luminar.V12 with Axiocam MRc5) equipped with an excitation source (365 nm) and an emission filter (400 nm long pass) was used to visualize positive compartments. The results are shown in Table 1.

Examples shown here were chosen because it is statistically likely (p<0.05) that only a single organism was partitioned from the original aqueous test solution into each well that yielded a positive fluorescence signal.

TABLE 1

Growth of $E.\ coli$ in a culture device according to the present disclosure.

|  | Example 1 (Growth-positive[a]) | PETRIFILM Plates (CFU) |
|---|---|---|
| Test Solution 1 (5 μL) | 21 compartments | 4 |
| Test Solution 2 (10 μL) | 130 compartments | 82 |

[a]Growth was evidenced by positive fluorescence and the absence of observable gas bubbles in each "growth-positive" compartment. Fluorescence in a compartment was considered positive for growth of the bacterium in the compartment.

In addition to using fluorescent indicators it was noticed that non-fluorescent wells had accumulated small gas bubbles during the incubation period while florescent wells (positive for growth) did not. The absence of bubbles in a compartment correlated with bacterial growth in the compartment.

Example 4: Detection of Bacterial Redox Activity and Growth

Stamped culture devices were prepared according to Example 1, using 0.1 or 0.01 mg/ml resazurin (Sigma-Aldrich Corp.; St. Louis, MO) instead of 0.5 mg/ml MUG (4-methylumbelliferyl-β-D-glucuronide). Addition of resazurin allows for detection of bacterial redox activity and does not rely on a specific enzyme activity (β-D-glucuronidase), as does MUG, to detect microbial activity.

The stamped culture devices were incubated as provided in Example 2 above. Aerobic count (AC) PETRIFILM plates were used as a comparator with 1 ml of the same test sample.

Detection of the bacterial growth was done by visual inspection of the liquid-filled compartments. Dark pink wells considered negative for bacterial growth and light pink to clear compartments were considered positive for bacterial growth. The results are shown in Table 2. As in Example 2 above, the absence of small gas bubbles within a compartment also was an accurate indicator of bacterial growth.

TABLE 2

|  | Example 3 (Growth-positive[a]) | PETRIFILM Plates (CFU) |
|---|---|---|
| 0.1 mg/ml Resazurin | 18 compartments | 4 |
| 0.01 mg/ml Resazurin | 24 compartments | 3 |

[a]Growth was evidenced by a color change and the absence of observable gas bubbles in each "growth-positive" compartment of Example 3.

Example 5: Time-to-Result for Detection of Continuous Growth of Bacteria

A culture device was constructed and inoculated as in Example 1 using the COLILERT® bacteriological medium (IDEXX laboratories; Westbrook, Maine) without added 4-methylumbelliferyl-β-D-glucuronide (MUG) since MUG is already contained within the COLILERT medium.

The device was positioned such that the compartments formed by the cover film were facing into the wells of a plastic 384-well microtiter plate (Untreated black #242764, Nalge Nunc International; Rochester, NY). This assembly was subsequently placed into the reading tray of a Tecan INFINITE® M200 plate reader (Tecan Systems, Inc., San Jose, CA) and scanned for fluorescence. In this configuration the light source and detector were above the device resulting in excitation and emission light passed through the substrate of the culture device.

The plate reader chamber was set to hold a temperature of 37° C. and fluorescence measurements were taken every 20 minutes for 24 hours using an excitation wavelength of 365 nm and an emission filter of 470±10 nm. The resulting fluorescence curves were plotted as a function of time. A compartment of the culture device was determined to be positive for growth when the fluorescence at any given time point was 2.5-fold greater than the average of the first 18 time points (6 hours) for that compartment. The time point (minutes of incubation at 37° C.) at which positive growth was observed in each compartment is reported in Table 3.

TABLE 3

Time to detection. This table reports the number of minutes of incubation required to observe positive growth in each compartment of a stamped culture device of the present disclosure.

| | | Column Number | | | | | | | | | | | |
|---|---|---|---|---|---|---|---|---|---|---|---|---|---|
| Row Number | | C | D | E | F | G | H | I | J | K | L | M | N | O |
| | 6 | — | — | — | — | — | 820 | 680 | NG | NG | — | — | — | — |
| | 7 | — | — | — | NG | 720 | 700 | 740 | 760 | 660 | NG | — | — | — |
| | 8 | — | NG | NG | 760 | 740 | 760 | 780 | 800 | 660 | NG | NG | NG | — |
| | 9 | — | 740 | NG | NG | 740 | 640 | NG | NG | NG | 840 | 780 | NG | — |

TABLE 3-continued

Time to detection. This table reports the number of minutes of incubation required to observe positive growth in each compartment of a stamped culture device of the present disclosure.

| Row Number | | C | D | E | F | G | H | I | J | K | L | M | N | O |
|---|---|---|---|---|---|---|---|---|---|---|---|---|---|---|
| | 10 | NG | NG | 660 | NG | NG | NG | NG | NG | NG | NG | 780 | NG | NG |
| | 11 | NG | 980 | NG | NG | NG | NG | 660 | 980 | NG | NG | 740 | 760 | 640 |
| | 12 | NG | 700 | NG | NG | NG | NG | 680 | 700 | 840 | 800 | NG | NG | NG |
| | 13 | 720 | 680 | 780 | 760 | 800 | 820 | 660 | 760 | NG | 680 | NG | 680 | NG |
| | 14 | NG | NG | 700 | 880 | NG | 700 | NG | NG | NG | NG | 760 | 700 | 640 |
| | 15 | NG | NG | NG | NG | 640 | NG | 740 | NG | 740 | NG | NG | 980 | — |
| | 16 | — | — | NG | NG | 680 | NG | 780 | 760 | NG | 740 | NG | NG | — |
| | 17 | — | — | — | 1140 | 660 | 700 | 720 | 640 | 680 | 700 | 840 | — | — |
| | 18 | — | — | — | — | 720 | NG | NG | 780 | 700 | NG | — | — | — |

"NG" = no growth (i.e., the fluorescence in the compartment did not exceed the stated threshold for determining microbial growth.

Rows and columns of the compartments are designated on the left side and top respectively. Numbers in each cell of the table indicate time-to-detection in minutes as outlined in Example 4. NG indicates no detectable growth for that well in 24 hours and "-" indicates unfilled wells, largely due to the circular shape of the stamped area.

In all, 65 wells out of 131 were positive for growth with an average time to detection of 747±11 minutes. Error calculation reflects the standard error of the mean. The median and mode time-to-detection were 740 and 700 minutes respectively and the range was 640 to 1140 minutes. The manufacturer stated time to detection for a single E. coli using COLILERT medium is 24 hours in a 100 ml sample and 18 hours using the QUANTI-TRAY® MPN system (IDEXX laboratories; Westbrook, Maine).

Example 6: Fabrication of a Pouch-Like Article and Partitioning of a Liquid Sample Therein Preparation of a Pouch The process for preparing a pouch is illustrated in FIGS. 4a-4e. A substrate 12 composed of biaxially oriented polypropylene was coated with a silicone based pressure sensitive adhesive (adhesive 15, FIG. 4a) as described in Example 1.

A mask (mask 70 of FIG. 4a) was constructed from a piece of polyethylene terephthalate (PET) release liner coated with a low-adhesion fluorosilicone backsize (available from Siliconature USA; Chicago, IL). The mask 70 had a 6 cm diameter circular opening 74 and a 1 cm wide gap 76 on one side of the perimeter 72 of the mask. The low-adhesion side of the mask 70 was placed onto the adhesive 15 coated on the substrate 12, as shown in FIG. 4b.

A secondary coating 18 of glass bubbles (K37 glass bubbles, 3M Company; St. Paul, Minnesota) was distributed onto the adhesive using a glass pasture pipette and a silicone bulb. Excess glass bubbles were removed by inverting and tapping the film, resulting in the coated article 200 shown in FIG. 4c. The mask 70 was then removed to expose the adhesive 15 that had been covered by the mask 70, as shown in FIG. 4d. A cover film 20 made from PARAFILM M plastic paraffin film, as described in Example 1, was adhered to the exposed adhesive 15, as described below.

A rubber roller was used to seal the cover film and substrate together in the areas where the adhesive was not powder-coated with glass bubbles. This effectively formed a pouch 500 having a circular reservoir 502 (FIG. 4e) with an inoculation port 504 on one side. Adhesion between the cover film and the substrate was effectively prevented where the glass bubbles had been coated onto the adhesive.

Inoculation and Partitioning of Sample in the Pouch Article.

Test solutions comprising a bacteriological medium with a 4-methylumbelliferyl-β-D-glucuronide fluorescent indicator (COLILERT medium, IDEXX laboratories; Westbrook, Maine) and Escherichia coli American Type Tissue Collection #25922 (EZ-CFU, Microbiologics; St. Cloud, Minnesota) were prepared as described in Example 1.

For inoculation the pouch was held upright with the inoculation port pointing upward. 1 ml of test solution was dispensed directly through the inoculation port into the pouch (as shown in FIG. 5a) and was allowed to settle at the bottom of the pouch.

The inoculated pouch was placed on an aluminum block at a 45° angle and a plastic spreading device (PETRIFILM yeast and mold plate spreader, 3M Company; St. Paul, Minnesota) was manually pressed against the pouch (with moderate manual pressure) to spread the liquid out and seal the liquid into a circular (6 cm diameter) chamber (chamber 90 bordered by perimeter seal 92, as shown in FIG. 5b) disposed between the cover film and the substrate. Spreading at a 45° angle, although not required, facilitated evacuation of air and uniform filling of the circular chamber as the pouch substrate was pressed against the cover film by the spreader. The spreader forced the cover film against the glass bubbles (not shown) driving the glass bubbles into the adhesive, thereby allowing the adhesive to contact the cover film to form the perimeter seal 92 between the substrate and the cover film.

A plastic 384-well microtiter plate (Untreated black #242764, Nalge Nunc International; Rochester, NY; tool 50 of FIG. 5c) was placed on top of the sealed pouch with the openings of the wells facing down and an air press (Model A-0019, Janesville Tool and Manufacturing, Inc.; Milton, WI) was used to press the microtiter plate down, deforming the cover film up into the cavities of the microtiter plate and sealing the cover film to the substrate to form the partitioned device 2000 having a plurality of compartments 60 with the liquid sample distributed therein. Each compartment 60 was fluidically isolated from the other compartments by one or more seal 62.

Examination of the sealed areas between the wells using a stereomicroscope revealed that the glass bubbles had been pushed down into the adhesive layer allowing the cover film to come into contact with the pressure sensitive adhesive.

Example 7: Fabrication of an Alternative Pouch-Like Article and Partitioning of a Liquid Sample Therein Preparation of a Pouch A pouch-like article was prepared as described in Example 6 with the exception that powdered bacteriological medium (BACTO Trypticase Soy Broth (Becton Dickinson and Company, Franklin Lakes, NJ) was used as the secondary coating instead of the glass bubbles.

A rubber roller was used to seal the cover film and the substrate together in the areas not powder coated with bacteriological medium, as described in Example 6. This effectively formed a circular pouch with an inoculation port along one edge, as described in Example 6. Adhesion between the cover film and the substrate was effectively prevented where the powdered bacteriological medium had been coated onto the adhesive.

Inoculation and Partitioning of Sample

For inoculation the pouch was held upright with the powder coated inoculation port pointing upward. 1 ml of test solution (comprising a bacteriological medium with a 4-methylumbelliferyl-β-D-glucuronide fluorescent indicator (COLILERT bacteriological medium, IDEXX laboratories; Westbrook, Maine) and *Escherichia coli* American Type Tissue Collection #25922) was dispensed directly into the pouch and allowed to settle at the bottom.

The inoculated pouch was sealed using a plastic spreading device (PETRIFILM yeast and mold plate spreader, 3M Company; St. Paul, Minnesota) as described in Example 6.

A plastic 384-well microtiter plate (Untreated black #242764, Nalge Nunc International; Rochester, NY) was used to complete the formation of the culture device comprising a plurality of compartments, as described in Example 6.

Visual inspection of the pouch before pressing and examination of the sealed areas between the wells using a stereoscope after pressing revealed that the powdered medium was dissolved by the addition of the test sample, re-exposing the adhesive, and allowing the cover film to come into contact with the pressure sensitive adhesive coated on the substrate.

The stamped culture device was placed in a 37° C. incubator.

Example 8: Growth of an Aerobic Microorganism in Compartments of a Stamped Culture Device—Quantitative and Qualitative Analysis A stamped culture device was prepared according to Example 1, using the culture medium, Heterotrophic Plate Count (HPC for QUANTI-TRAY medium) (IDEXX laboratories; Westbrook, Maine) and *Pseudomonas aeruginosa* ATCC #15442 (American Type Tissue Collection; Manassas, Virginia) as the test microorganism.

Culture devices were inoculated and incubated at 37° C. for 24 hours as described in Examples 1-3. Aerobic count (AC) PETRIFILM plates (3M Company; St. Paul, MN) were used as a comparator with 1 ml of the same test solution having been inoculated onto the PETRIFILM plates, spread, and incubated at 37° C. for 24 hours.

After the 24 h of incubation, the compartments of the stamped culture devices were assessed for growth of bacteria. A stereomicroscope (Zeiss Luminar.V12 with Axiocam MRc5) equipped with an excitation source (365 nm) and an emission filter (400 nm long pass) was used to observe each compartment for fluorescence, described above. The results are shown in Table 4.

TABLE 4

| Example 8 (Growth-positive[a]) | PETRIFILM Plates (CFU) |
|---|---|
| 34 compartments | 24 |

[a]Growth was evidenced by positive fluorescence in each "growth-positive" compartment of Example 8.

The data demonstrate the growth and enumeration of aerobic bacteria in the stamped culture device.

Example 9: Growth of an Anaerobic Microorganism in Compartments of a Stamped Culture Device—Quantitative and Qualitative Analysis A stamped culture device was prepared according to Example 1, using the culture medium, 37 g/L Brain Heart Infusion Broth, 5 g/L BACTO Yeast Extract (Becton, Dickinson and Company; Franklin Lakes, New Jersey), 0.5 g/L cysteine hydrochloride, 0.5 g/L sodium sulfite, and 0.5 g/L iron sulfate (Sigma Aldrich; St. Louis, MO).

*Clostridium sporogenes* ATCC #5384 (American Type Tissue Collection; Manassas, Virginia) was chosen as the microorganism to demonstrate the growth of an anaerobic microorganism in the stamped culture devices in conjunction with an anaerobic atmosphere system.

Culture devices were inoculated and incubated in a sealed box with an activated GASPAK™ EZ Anaerobe Container System Sachet w/Indicator (Becton, Dickinson and Company; Franklin Lakes, New Jersey) at 37° C. for 24 hours.

Aerobic count (AC) PETRIFILM plates (3M Company; St. Paul, MN) were used as a comparator with 1 ml of the same test solution having been inoculated onto the film, spread, and incubated at 37° C. for 24 hours in the same anaerobic container as the stamped culture devices (Table 5).

Figure 6:
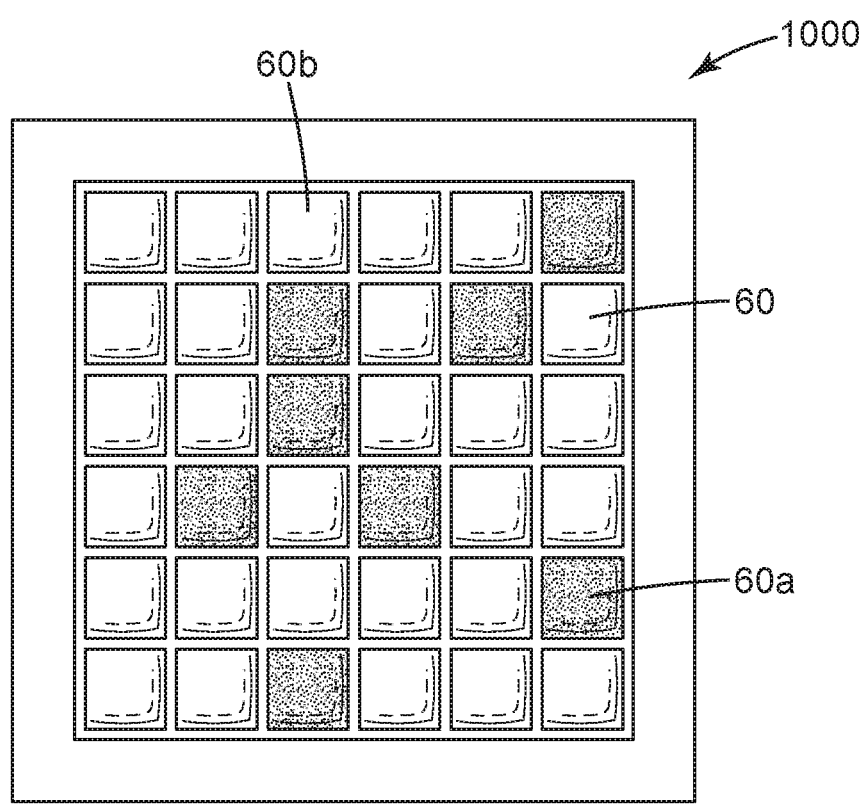
FIG. 6 is a schematic plan view of one embodiment of the use of the device of FIG. 2d to detect a microorganism.

After the incubation period, compartments in the stamped culture device that contained a black precipitate, resulting from the reaction of hydrogen sulfide produced by *Clostridium sporogenes* ATCC #5384 with the iron present in the medium, were considered positive for growth (Table 5). It is observed that there is good growth of anaerobic bacterium in the stamped culture device as shown in Table 5. FIG. 6 shows a schematic top view of a stamped culture device 1000 having a plurality of compartments 60. The shaded compartments 60a indicate an observable (e.g., visible color change) reaction with an indicator substance (e.g., the iron present in the medium of Example 9). The unshaded compartments 60b indicate no observable reaction with the indicator substance.

TABLE 5

| | Example 9 (Growth-positive[a]) | PETRIFILM Plates (CFU) |
|---|---|---|
| Test Solution 1 | 65 compartments | 45 |
| Test Solution 2 | 9 compartments | 8 |

[a]Growth was evidenced by a black precipitate in each "growth-positive" compartment of Example 9.

Example 10: Performance of Secondary Biochemical Test

Stamped culture devices were prepared and inoculated with HPC medium as described in Example 2.1. One set of the devices was inoculated with *Pseudomonas aeruginosa* ATCC #15442 and another set of culture devices was inoculated with *Escherichia coli* ATCC #25922. Both sets were incubated at incubated 37° C. for 24 hours.

After incubation, the compartments of each culture device were observed under u.v. illumination to detect growth. Positive fluorescence (growth) was observed in at least several compartments of each culture device (i.e., both *Pseudomonas aeruginosa* and *Escherichia coli* samples produced fluorescence-positive compartments.

Representative fluorescence-positive compartments from each culture device were pierced with a capillary pipet containing 30% $H_2O_2$ (Sigma Chemical Co.). Some wells were pierced through the (foil) substrate. Others were pierced through the cover film. In all cases, fluorescent-positive compartments in the devices inoculated with *Pseudomonas aeruginosa* produced a vigorous bubbling reaction with the peroxide solution. In contrast, all cases, fluorescent-positive compartments in the devices inoculated with *Escherichia coli* did not produce any observable bubbling reaction when the peroxide solution was introduced into the compartments.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A method of incubating and analyzing a liquid comprising
    depositing a liquid device onto a first surface of a substrate of a device such that the liquid sample is disposed between the first surface and a polymeric cover film wherein said first surface is coated with water-insoluble pressure sensitive adhesive;
    wherein the polymeric cover film is a composite film comprising a polymer and a tackifier;
    urging an external means against the cover film to bring discrete regions of the cover film in contact with the pressure sensitive adhesive of the substrate resulting in the partitioning of the liquid into a plurality of closed compartments disposed between the substrate and the cover film;
    incubating the liquid under conditions that facilitate at least one cell division and
    conducting a most probable number analysis for a microorganism in the device.

2. The method of claim 1, wherein the most probable number analysis is conducted on the liquid within the plurality of closed compartments a single device.

3. The method of claim 1, wherein the microorganisms is *E. coli* or *S. aureus*.

4. The method of claim 1, wherein the plurality of closed compartments are microcompartments, each having a volume that is a microvolume.

5. The method of claim 1, wherein the device comprises 100 to 300 closed compartments and the method comprises partitioning the liquid among in the 100 to 300 closed compartments.

6. The method of claim 1, further comprising urging an external means against the cover film to bring regions of the cover film in contact with the pressure sensitive adhesive on the substrate.

7. The method of claim 1, wherein the method does not comprise performing serial dilutions on the liquid.

8. The method of claim 1, wherein the method does not include a step of cross-contaminating between the plurality of closed compartments.

9. The method of claim 1, further comprising placing a base of the device in contact with a compliant surface while bringing regions of the cover film in contact with the pressure sensitive adhesive.

10. The method of claim 1, wherein the step of bringing regions of the cover film in contact with the pressure sensitive adhesive seals the plurality of closed compartments comprises sealing the plurality of closed compartments.

11. The method of claim 9, wherein the base of the device comprises a compliant member.

12. The method of claim 1, wherein the plurality of closed compartments comprise a nutrient growth medium.

13. The method of claim 12, wherein the nutrient growth medium is a selective growth medium.

14. The method of claim 12, wherein the nutrient growth medium comprises at least one indicator substance.

15. The method of claim 1, wherein the microorganism is an anaerobic microorganism and the device is kept in an anaerobic environment during the incubation step.

16. The method of claim 1, wherein the step of incubating is conducted at 25° C. to 45° C.

* * * * *